United States Patent [19]
Seilhammer et al.

[11] Patent Number: 6,153,195
[45] Date of Patent: *Nov. 28, 2000

[54] METHOD OF DELIVERING DRUGS TO CELLS SPECIFIC FOR AN HL-60 LECTIN

[75] Inventors: Jeffrey J. Seilhammer, Milpitas; Glenn Nedwin, Davis; Tim Bringman, Solana Beach, all of Calif.; Pierre-Olivier Couraud, Auffargis, France

[73] Assignee: Incyte Pharmaceuticals, Inc., Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/719,866

[22] Filed: Sep. 25, 1996

Related U.S. Application Data

[62] Division of application No. 08/326,739, Oct. 20, 1994, Pat. No. 5,693,760, which is a continuation of application No. 07/976,928, Nov. 16, 1992, abandoned, which is a continuation-in-part of application No. 07/313,649, Feb. 21, 1989, abandoned, which is a continuation-in-part of application No. 07/263,734, Oct. 28, 1988, abandoned, which is a continuation-in-part of application No. 07/181,747, Apr. 14, 1988, abandoned.

[51] Int. Cl.$^7$ .......................... A61K 45/00; A61K 35/12; C07K 14/435; C07K 14/47

[52] U.S. Cl. ...................... 424/193.1; 424/184.1; 424/185.1; 514/2; 514/8; 530/350; 530/395; 530/396

[58] Field of Search ................ 424/184.1, 185.1

[56] References Cited

U.S. PATENT DOCUMENTS

| | | |
|---|---|---|
| 4,786,592 | 11/1988 | Deal . |
| 5,225,542 | 7/1993 | Cramer et al. . |
| 5,258,287 | 11/1993 | Baxter et al. . |

FOREIGN PATENT DOCUMENTS

| | | |
|---|---|---|
| 0260497 | 3/1988 | European Pat. Off. . |
| 60-184020 | 9/1985 | Japan . |
| WO8900581 | 1/1989 | WIPO . |

OTHER PUBLICATIONS

Tufveson et al. Immunol. Reviews 136:99–109, 1993.
Dijkstra, C. et al. TIPS 14: 124–129, Apr. 1993.
Rudinger, J. in Peptide Hormones, Parsons, J. A. (Ed.), University Park Press, Baltimore, MD, pp. 1–7, Jun. 1976.
Rabinovich, A. Diabetes 43: 613–621, May 1994.
Gilliland, D. G. et al. J. Biol. Chem. 256 (24): 12731–12739, Dec. 25, 1981.
Hafler, D. A. et al. Neurology 36: 777–784, Jun. 1986.
Rawlins, E.A., *Bentley's Textbook of Pharmaceutics*, pp. 186, 192–194 (1978) Bailliére Tindall (London).
Sharon, "Lectins: An overview" *Vertebrate Lectins* Olden, K., et al., eds., pp. 27–32 (1987) Van Nostrand Reinhold Advanced Cell Biology Series (NY).

Liener, et al., *The Lectins:Properties, Functions and Applications in Biology and Medicine*, p. 353 (Mar. 2, 1986) Academic Press (NY).
Goding, J.W., *Monoclonal Antibodies: Principles and Practice*, pp. 250–261 (1983) Academic Press (NY).
Sparrow et al., "Multiple soluble β–galactoside–binding lectins from human lung", *J. Biol. Chem.* (1987) 262(15):7383–7390.
Roff et al., "Endogenous lectins from cultured cells", *J. Biol. Chem.* (1983) 258(17):10657–10663.
Cerra et al., "Three soluble rat β–galactoside–binding lectins", *J. Biol. Chem.* (1985) 260(19):10474–10477.
Beyer et al., "Two lactose binding lectins from chicken tissues", *J. Biol. Chem.* (1980) 255(9):4236–4239.
Gitt et al., "Evidence that a human soluble β–galactoside–binding lectin is encoded by a family of genes", *Proc. Natl. Acad. Sci.* (1986) 83:7603–7607.
Ohyama et al., "Nucleotide sequence of chick 14K β–galactoside–binding lectin mRNA", *Biochem. Biophys. Res. Comm.* (1986) 134(1):51–56.
Caron et al., "Purification and characterization of a β–galactoside–binding soluble lectin from rat and bovine brain", *Biochim. Biophys. Acta* (1987) 925:290–296.
Fink de Cabutti et al., "Purification and some characteristics of a β–galactoside binding soluble lectin from amphibian ovary", *Federation of European Biochemical Societies Letters* (1987) 223(2):330–334.
Levi et al., "Isolation and physiochemical characterization of electrolectin, a β–D–galactoside binding lectin from the electric organ of electrophorus electricus", *J. Biol. Chem.* (1981) 256(11):5735–5740.
Raz et al., "Cloning and expression of cDNA for two endogenous UV–2237 fibrosarcoma lectin genes", *Experimental Cell Research* (1987) 173:109–116.

(List continued on next page.)

*Primary Examiner*—Phillip Gambel
*Attorney, Agent, or Firm*—Dianna L. DeVore; Bozicevic, Field & Francis LLP

[57] ABSTRACT

Pharmaceutical compositions useful in the treatment of autoimmune conditions include as an active ingredient a soluble lectin having a molecular weight of about 14 kilodaltons or a fragment thereof. The lectin or fragment binds β-galactoside-containing moieties independent of the presence or absence of $Ca^{+2}$, stimulates hemagglutination of trypsinized rabbit erythrocytes in standard lectin assays wherein the stimulation is inhibited by lactose or thiogalactoside, has an amino acid sequence containing at least one N-glycosylation site and is at least 90% homologous to the amino acid sequence shown in positions 2–135 of FIG. 1 or the relevant portions thereof. The composition is used for treatment of autoimmune conditions such as rheumatoid arthritis, myasthenia gravis, and multiple sclerosis, as well as modulating the immune response in an allergic reactions or to organ or tissue transplant rejection. The inventive composition can be combined with general immunosuppressants. Drugs can be delivered by coupling the lectin to a drug to form a lectin-drug complex and administering the lectin-drug complex to a subject.

2 Claims, 11 Drawing Sheets

OTHER PUBLICATIONS

Clerch et al., "Sequence of a full–length cDNA for rat lung β–galactoside–binding protein: primary and secondary structure of the lectin", *Biochem.* (1988) 27:692–699.

Joubert et al., "Brain lectin–mediated agglutinability of dissociated cells from embryonic and postnatal mouse brain", *Developmental Brain Research* (1987) 36:146–150.

Raz et al., "Lectin–line Activities Associated with Human and Murine Neoplastic Cells", *Cancer Research* (1981) 41:3642–3647.

Paroutaud et al., "Extensive amino acid sequence homologies between animal lectins", *Proc. Natl. Acad. Sci.* (1987) 84:6345–6348.

Paietta et al., "A membrane–bound lectin responsive to monocytic maturation in the promyelocytic leukemia cell line HL–60", *Cancer Research* (1988) 48:280–287.

Levi et al., "Prevention and therapy with electrolectin of experimental autoimmune myastenia gravis in rabbits", *Eur. J. Immunol.* (1983) 13:500–507.

Wraith et al., "T cell recognition as the target for immune intervention in autoimmune disease", *Cell* (1989) 57:709–715.

Drickamer, "Two distinct classes of carbohydrate–recognition domains in animal lectins", *J. Biol. Chem.* (1988) 263(20):9557–9560.

Hirabayashi et al., "Complete amino acid sequence of a β–galactoside–binding lectin from human placenta", *J. Biochem.* (1988) 104:1–4.

Hirabayashi et al., "Complete amino acid sequence of 14 kDa β–galactoside–binding lectin of chick embryo", *J. Biochem.* (1987) 101:775–787.

Leffler et al., "Specificity of binding of three soluble rat lung lectins to substituted and unsubstituted mammalian β–galactosides", *J. Biol. Chem.* (1986) 261(22):10119–10126.

Powell et al., "Purification and properties of lung lectin: Rat lung and human lung β–galactoside–binding proteins", *Biochem. J.* (1980) 187:123–129.

Hirabayashi et al., "Further characterization and structural studies on human placenta lectin", *J. Biochem.* (1987) 101 (4):987–995.

Lempfrid et al., "Lectinreceptor–mediated endocytosis of helix pomatia lectin by zajdela hepatoma cells", in *Lectins: Biology, Biochemistry, Clinical Biochemistry, Volume 3*, (Proceedings of the Fifth Lectin Meeting, Bern, Bog–Hansen and Spengler, eds., Walter de Gruyter, Berlin, New York, 1983) pp. 73–84.

Fudenberg et al., "Chapter 39: Experimental Immunotherapy", in *Basic & Clinical Immunology*, (5th Edition, Stites et al., eds., Lange Medical Publications, Los Altos, California, 1984) p. 756.

Hirabayashi et al., "Human placenta β–galactoside–binding lectin. Purification and some properties", *Biochem. Biophys. Res. Comm.* (1984) 122(3):938–944.

Couraud et al., "Molecular cloning, characterization, and expression of a human 14–kDa lectin", *J. Biol. Chem.* (1989) 264(2):1310–1316.

Weber et al., "The reliability of molecular weight determinations by dodecyl sulfate–polyarcylamide gel electrophoresis", *J. Biol. Chem.* (1969) 244(16):4406–4412.

FIG. 1

```
          10        20        30        40        50
CTTCTGACAGCTGGTGCCGCCTGCCCGGGAACATCCTCCTGACTCAATC ATG GCT
                                                   Met Ala
 60          70          80          90         100        110
TGT GGT CTG GTC GCC AGC AAC CTG AAT CTC AAA CCT GGA GAG TGC CTT CGA GTG CGA
Cys Gly Leu Val Ala Ser Asn Leu Asn Leu Lys Pro Gly Glu Cys Leu Arg Val Arg 120         130         140         150         160
GGC GAG GTG GCT CCT GAC GCT AAG AGC TTC GTG CTG AAC CTG GGC AAA GAC AGC AAC
Gly Glu Val Ala Pro Asp Ala Lys Ser Phe Val Leu Asn Leu Gly Lys Asp Ser Asn 170         180         190         200         210         220
AAC CTG TGC CTG CAC TTC AAC CCT CGC TTC AAC GCC CAC GGC GAC GCC AAC ACC ATC
Asn Leu Cys Leu His Phe Asn Pro Arg Phe Asn Ala His Gly Asp Ala Asn Thr Ile 230         240         250         260         270         280
GTG TGC AAC AGC AAG GAC GGG AGT GTT GCA GAG TAC TTC ACC ATC GAC TTC GTC TTT
Val Cys Asn Ser Lys Asp Gly Ser Val Ala Glu Tyr Phe Thr Ile Asp Phe Val Phe 290         300         310         320         330         340
CCC TTC CAG CCT GGA AGT GTT GCA GAG TAC TTC ACC ATC GAC TTC CAG GCC AAC CTG
Pro Phe Gln Pro Gly Ser Val Ala Glu Tyr Phe Thr Ile Asp Phe Gln Ala Asn Leu
                                                                          *

350         360         370         380         390
ACC GTC AAG CTG CCA GAT GGA TAC GAA TTC AAG TTC CCC AAC CGC CTC AAC CTG GAG
Thr Val Lys Leu Pro Asp Gly Tyr Glu Phe Lys Phe Pro Asn Arg Leu Asn Leu Glu 400         410         420         430         440         450
GCC ATC AAC TAC ATG GCA GCT GAC GGT GAC TTC AAG ATC AAA TGT GTG GCC TTT GAC
Ala Ile Asn Tyr Met Ala Ala Asp Gly Asp Phe Lys Ile Lys Cys Val Ala Phe Asp 460         470         480         490         500
TGA AATCAGCCAGCCCATGGCCCCCAATAAAGGCAGCTGCCTCTGCTCCCCTG
```

Anti-HML-1
FITC

Anti-cytokeratin
TRITC

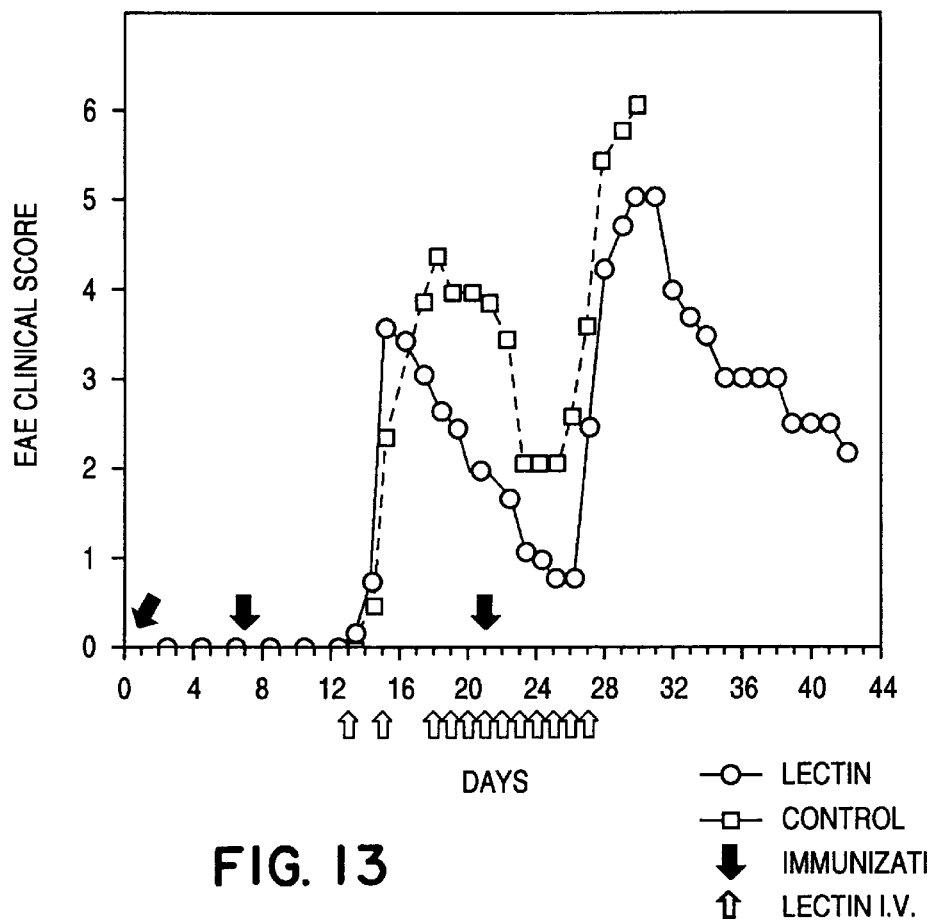
FIG. 13
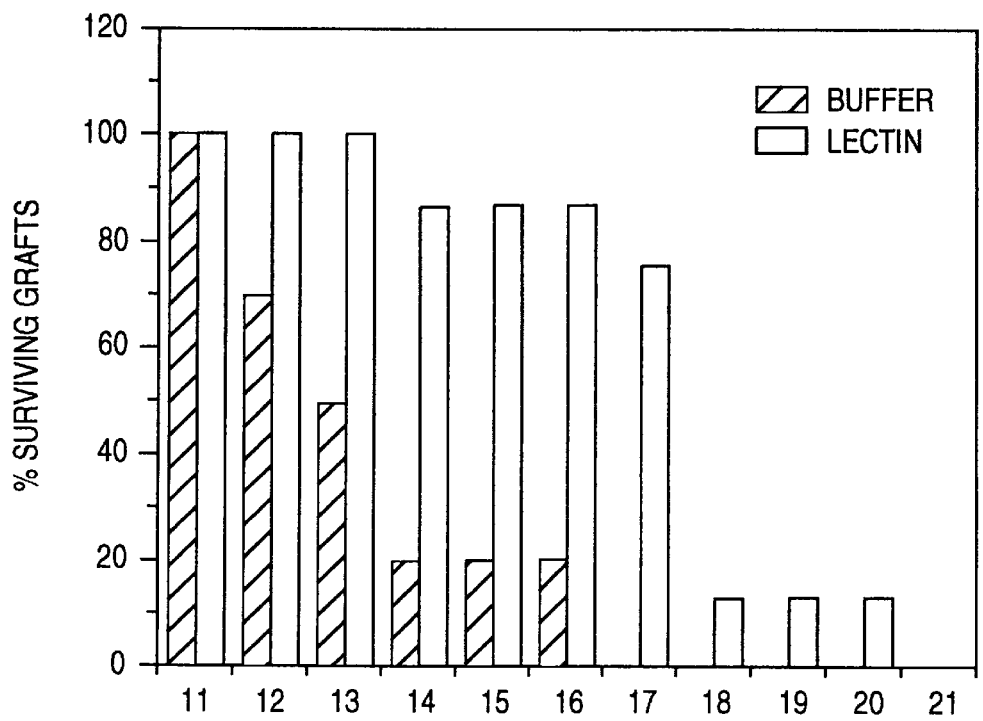
FIG. 14  DAYS AFTER GRAFT

METHOD OF DELIVERING DRUGS TO CELLS SPECIFIC FOR AN HL-60 LECTIN

CROSS-REFERENCE TO RELATED APPLICATIONS

This application is a divisional of application Ser. No. 08/326,739 filed Oct. 20, 1994, now U.S. Pat. No. 5,693,760, which is continuation of application Ser. No. 07/976,928 filed Nov. 16, 1992 (Abandoned), which is a continuation-in-part of application Ser. No. 07/313,649 filed Feb. 21, 1989 (Abandoned), which is a continuation-in-part of application Ser. No. 07/263,734 filed Oct. 28, 1988 (Abandoned), which is a continuation-in-part of application Ser. No. 07/181,747 filed Apr. 14, 1998 (Abandoned).

TECHNICAL FIELD

The invention relates to the use of carbohydrate-binding proteins as regulators of cell differentiation and immunity. In particular, it concerns a pharmaceutical composition where the active ingredient is a soluble lectin of about 14 kD or a fragment thereof which can be isolated from human HL-60 cells or placenta tissue. Recombinant materials and methods to produce these inventive lectins are also provided. This invention is also directed to methods to treat autoimmune diseases and to prevent transplant rejection.

BACKGROUND ART

Lectins are defined as proteins which specifically bind carbohydrates of various types. Initial interest was focused on those isolated from plants such as concanavalin A and ricin agglutinin. These lectins, it was found, were useful in protein purification procedures due to the glycosylation state of a number of proteins of interest. Among the soluble lectins, there appear to be a number of varieties with varying molecular weights and/or carbohydrate specificities. Sparrow, C. P., et al., *J. Biol. Chem.* (1987) 252:7383–7390 describe three classes of soluble lectins from human lung, one of 14 kD, one of 22 kD, and a third of 29 kD. All of these lectins are specific to β-D-galactosides. The carbohydrate specificities of the 14 kD class are for the most part similar, but the larger molecular weight species tend to have different specificities. Other species are also noted as showing more than one soluble β-D-galactoside-binding lectin, including mouse (Roff, C. F., et al., *J. Biol. Chem.* (1983) 258:10637–10663); rat (Cerra, R. F., et al., *J. Biol. Chem.* (1985) 260:10474–10477) and chickens (Beyer, E. C., et al., *J. Biol. Chem.* (1980) 255:4236–4239). Among the various β-D-galactoside-specific soluble lectins, ligand specificity is considerably different, and the approximately 14 kD group appears distinct from the 22 kD and 29 kD representatives described by Sparrow, et al., supra.

Recently, however, interest has focused on a group of lactose-extractable lectins which bind specifically to certain β-D-galactoside containing moieties and are found in a wide range of mammalian, in-vertebrate, avian, and even microbial sources. All of the lectins in this class appear to contain subunits with molecular weights of about 12–18 kD. Furthermore, these lectins can be readily classified by virtue of a simple diagnostic test: their ability to agglutinate trypsin-treated rabbit red blood cells is specifically inhibited by certain β-D-galactose-containing moieties. Thus, although the lectins themselves agglutinate trypsinized rabbit erythrocytes, the agglutination can be inhibited by, for example, lactose, thiodigalactoside and certain other β-D-galactose containing moieties. Other common characteristics include no requirement for metal ions in effecting agglutination and the required presence of a reducing agent such as a thiol.

Gitt, M. A. et al., *Proc. Natl. Acad. Sci. U.S.A.* (1986) 83:7603–7607 obtained two cDNA clones from immuno-screening a human hepatoma cDNA library with an antiserum specific to a human lung lectin. Gitt et al. partially sequenced the cDNAs and the lectins. Gitt compared these sequences with that of the human lung chicken lectin. Although there were marked similarities with chicken and lung lectin, Gitt et al. concluded "In contrast with lung [encoding one form of HL-14 lectin], human hepatoma appears to express two other forms of HL-14" (page 7607). Kasai, K. et al., in Japanese Kokai 60/184020 describe a human placental lectin of approximately 14 kD. The sequence of this placental lectin was shown by the same group to be somewhat similar to that isolated from chick tissues (Ohyama, Y., et al., *Biochem. Biophys. Res. Commun.* (1986) 134:51–56). The chick-derived lectin was shown to be similar in structure to that of discoidin I, which is a lectin also observed during certain developmental stages of the cellular slime mold *Dictyostelium discoideum*.

Caron, M., et al., *Biochim. Biophys. Acta* (1987) 925:290–296 describe the purification and characterization of lectins from rat and bovine brain tissue. deCabutti, N. E. F., et al., *FEBS Letters* (1987) 223:330–334 describe a lectin from amphibian ovary. The isolation from eel of a similar "electrolectin" had previously been described by Levi, G., et al., *J. Biol. Chem.* (1981) 256:5735–5740. An additional analogous 14 kD lectin was produced by cloning and expression of cDNA derived from various murine fibrosarcoma cell lines by Raz, A., et al., *Experimental Cell Research* (1987) 173:109–116. A rat lung 14 kD lectin, and the cDNA encoding it were described by Clerch, L. B., et al., *Biochemistry* (1988) 27:692–699. Joubert, R., et al., *Develop. Brain Res.* (1987) 36:146–150 describe the isolation of lectins from rat brain which are capable of agglutinating brain cells. Raz, A., et al., *Cancer Res.* (1981) 41:3642–3647 describe a variety of lectins from neoplastic cells of various mammalian species.

Paroutaud, P., et al., (*Proc. Natl. Acad. Sci. U.S.A.* (1987) 84:6345–6348) compared the amino acid sequences of several animal lectins including those from chick, eel, human placenta, human lung, and two hepatoma-derived lectins (all of these lectins described as referenced above). Only the chicken lectin contains an "N-linked" glycosylation site, which is not conjugated to saccharide. No known mammalian lectin in this family has an N-linked glycosylation site.

Although several of the above references disclose some structural similarities with the present invention, none of the references teach the same bioactivity of the unique lectin of the present invention.

The preferred lectins of the present invention are isolated from the human promyelocytic leukemia cell line HL-60 or human placenta tissue. Lectins have been isolated from the HL-60 cell line by others, but they are markedly different from the lectins of the present invention. Paietta, E., et al., *Cancer Res.* (1988) 48:280–287 describe a membrane-bound (not soluble), 17 kd lectin which recognizes N-acetyl neuraminic acid as well as galactose terminating biantennary oligosaccharide structures. Unlike other 14 kd lectins, this 17 kd lectin is not inhibited by complex galactose saccharides such as thiodigalactoside and does not require reducing thiol groups for binding activity.

Thus, ligand specificity and biodistribution of the lectin protein described herein are an abrupt departure from the earlier disclosed lectins.

Because the activities of lectins in regulating the immune system and mediating other forms of intercellular communication are so subtle in nature and so critically tuned to the host environment, subtle changes in structure can result in a wide range of such regulators with differing therapeutic and diagnostic uses. As described above, a number of members of the class of β-D-galactose-binding soluble lectins weighing approximately 14 kD are known in the art. However, while these lectins have some similarities, they are not interchangeable therapeutically or diagnostically. In addition, it appears that for lectins which can be glycosylated, the extent and nature of the glycosylation can be manipulated to alter important lectin properties (e.g., circulating half-life, metabolism in vivo, solubility, stability, and specific activity).

Levy et al. (*Eur. J. Immunol.* (1983) 13:500–507) reported that electrolectin binds to peripheral blood and lymph node lymphocytes and is mitogenic. When Levy et al. administered electrolectin to rabbits simultaneously with acetylcholine receptor, it prevented the development of a myasthenia gravis-like condition. Administering electrolectin after development of myasthenia gravis caused complete recovery, in spite of high antibody levels specific for the acetylcholine receptor. Because electrolectin did not interfere with acetylcholine interaction with its receptor, Levy et al. proposed that electrolectin had an effect on the immune system.

Prominent diseases in which there is an immune system dysfunction include autoimmune diseases such as myasthenia gravis (MG), rheumatoid arthritis (RA) systemic lupus erythematosus (SLE), multiple sclerosis (MS) and juvenile arthritis. Typically MG, RA, SLE and MS are treated first with corticosteroids. Steroidal drugs have been used for decades and their adverse effects are well known. Adverse effects that can be anticipated in all patients on prolonged steroid therapy include osteoporosis, truncal obesity, impaired wound healing, infections and growth arrest in children. Less frequently occurring adverse effects include myopathy, hypertension, hyperlipidemia, diabetes mellitus and cataracts. Severe side effects may develop and require patient monitoring. These include glaucoma, intracranial hypertension, intestinal perforation, and ulcers.

If MG, RA, SLE or MS become refractory to steroids, then increasingly toxic drugs are employed, including azathioprine, methotrexate and cyclophosphamide. The primary effect of azathioprine is inhibiting DNA synthesis, thus lowering numbers of T and B lymphocytes. In addition, azathioprine inhibits the mixed lymphocyte reaction and immunoglobulin production, but does not consistently affect delayed-type hypersensitivity. The major adverse effect of azathioprine is pancytopenia, particularly lymphopenia and granulocytopenia. Consequently, there are increased risks of viral, fungal, mycobacterial and protozoal infections. An increased rate of lymphoreticular malignancies has been reported in kidney transplant patients, but not in patients with RA.

Methotrexate inhibits folic acid synthesis and is cytotoxic, suppressing bone marrow. At the low doses used for RA, methotrexate should not decrease the numbers of lymphocytes; but IgM and IgG are reduced. Side effects include pneumonia, nausea, stomach upsets, mouth ulcers, leukopenia, thrombocytopenia, and a form of hepatic fibrosis, which can only be diagnosed by liver biopsy.

Cyclophosphamide is also used in RA therapy. It is metabolized in the liver to a compound which cross-links DNA. Cyclophosphamide is cytotoxic, with severe toxicity seen even at low doses. It affects RA by reducing numbers of B- and T-lymphocytes, decreasing the immunoglobulin concentrations and diminishing B-cell responsiveness to mitogenic stimuli. Hair loss, infections, and powerful nausea are common. With prolonged administration, patients develop malignancies at an increased rate.

Cyclosporin does not suppress white cells, but it is a powerful immunomodulatory drug and is effective in treating rheumatoid arthritis. However, an important side effect is renal toxicity.

Monoclonal antibodies to CD4 have been used in autoimmune diseases, but they cause nonspecific immunosuppression. It has been recommended that new therapies interfere with the initial presentation of specific inciting antigens to T-lymphocytes. (Wraith et al., *Cell* (1989) 57:709–715).

Other drugs have been used specifically in RA, including gold salts, antimalarials, sulfasalazine and penicillamine. Gold salts are given intramuscularly and their effect may not be seen for months. Adverse effects of gold treatment include bone marrow aplasia, glomerulonephritis, pulmonary toxicity, vasomotor reactions and inflammatory flare. Antimalarials exert several effects on the immune system without decreasing the numbers of lymphocytes. The most serious side effects of antimalarials include retinal pigment deposition, rash and gastrointestinal upset. Sulfasalazine has several effects which contribute to its effect on RA; however, it has numerous side effects. Penicillamine has been successfully used in RA; however, its numerous side effects have limited its use. Penicillamine has been reported to cause other autoimmune diseases, including myasthenia gravis and SLE.

When patients receive allografts (transplanted tissue from other humans or other sources), their immune systems can destroy the allografts in short order were it not for the administration of immunosuppressant drugs. A number of different organs and tissues are now transplanted, including the kidneys, heart, lungs, skin, bone marrow, cornea, and liver. Drugs frequently used in transplant patients include cyclosporin, azathioprine, rapamycin, other macrolides such as FK506, prednisone, methylprednisolone, CD4 antibodies and cyclophosphamide. Frequently these drugs must be given in higher doses and for longer periods to transplant patients than to patients with autoimmune diseases. Hence, side effects from these drugs (discussed above) may be more common and severe in transplant patients.

What was needed before the present invention is a drug that would selectively treat autoimmune diseases and transplant rejection without the severe side effects of the previously known therapies.

SUMMARY OF THE INVENTION

The present invention is directed to a pharmaceutical composition. The active agent is a soluble lectin of MW of about 14 kD or a fragment thereof, wherein the lectin or fragment (1) binds β-galactoside-containing moieties whether $Ca^{+2}$ is present or not, (2) stimulates hemagglutination of trypsinized rabbit erythrocytes in standard lectin assays which is inhibited by lactose or thiodigalactoside, (3) provides an amino acid sequence containing at least one N-glycosylation site and at least 90% homologous to the amino acid sequence shown in positions 2–135 of FIG. 1 or the relevant portions thereof, and wherein the active ingredient is mixed with a carbohydrate and at least one pharmaceutically acceptable excipient. The composition can also contain one or more general immune system suppressants such as cyclosporin. The invention also provides recombinant materials and methods to produce these new lectins.

In other aspects, the invention is directed to methods to treat autoimmune diseases and to prevent transplant rejection. The efficacy of these methods results from the surprising ability of the inventive lectin to suppress the host immune response to both autoimmunogens and foreign tissue.

BRIEF DESCRIPTION OF THE DRAWINGS

FIG. 1 shows the cDNA sequence and deduced amino acid sequence of both the HL-60 and placenta lectin. Superscript numbers correlate to the corresponding nucleotides and boxes show start and stop codons. The asterisk indicates the possible N-linked glycosylation site.

FIG. 13 shows the effect of the recombinantly produced lectin on a relapse murine model for multiple sclerosis.

FIG. 14 is a graphical comparison of the survival of skin allografts when rats received lectin and placebo.

BEST MODES OF CARRYING OUT THE INVENTION

The Inventive Compositions

Figure 2A:
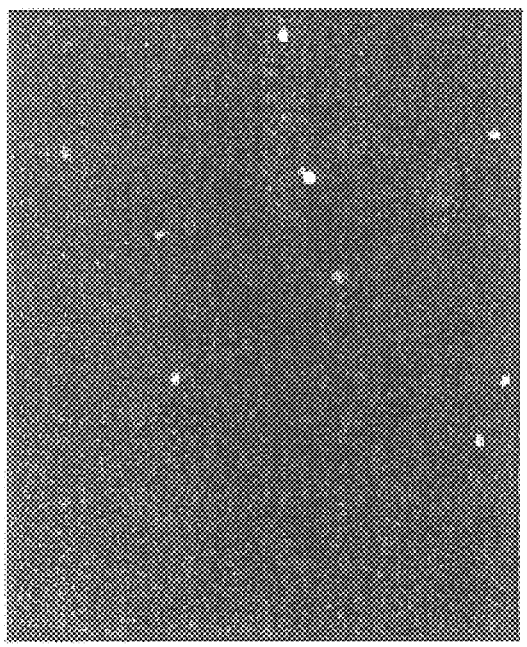
FIG. 2 shows immunostaining of thymic epithelium by anti-lectin and anti-cytokeratin antibodies.

The invention is directed to pharmaceutical compositions wherein the active ingredient is a soluble, 14 kD lectin or fragment thereof. The preferred lectin of the invention is isolatable from HL-60 cells as well as from human placental tissue. The lectins of this invention are soluble, capable of binding β-galactoside-containing moieties independent of the presence or absence of calcium ion, capable of stimulating hemagglutination of trypsinized rabbit erythrocytes in standard lectin assays which can be inhibited by lactose or thiogalactoside, and at least 90% homologous to the relevant portion of positions 2–135 of FIG. 1. One embodiment consists essentially of the amino acids shown in FIG. 1 numbered from 2–135 which contain at least one tripeptide sequence, Asn-X-Thr or Asn-X-Ser. Preferably, this tripeptide sequence provides a glycosylation site. In native production by HL-60 cells and placental tissue, the N-terminal methionine of the HL-60 lectin appears to be cleaved, and the remaining protein can be acetylated. Various forms of post-translational processing can be expected depending on the cell producing the protein. The processed proteins resulting therefrom are, of course, included within the scope of the invention.

In particular, it should be noted that unlike the prior art mammalian lectins whose protein sequences are known, a preferred embodiment of this invention provides a lectin with at least one glycosylation site, exemplified by Asn-Leu-Thr. Most preferably, the glycosylated tripeptide starts at position 96 of the illustrated HL-60 lectin. The native material, at least in part, apparently is not glycosylated at this site; however, when the lectin is appropriately produced in certain recombinant hosts, the site can be glycosylated. Accordingly, the invention provides for glycosylated forms, so long as glycosylation does not destroy activity.

The preferred lectins include the peptide comprising positions 2–135 in FIG. 1 or the naturally occurring mutants or allelic variations thereof. It is well understood that proteins produced by organisms do not necessarily remain stable in the form studied, but that the genes encoding them are subject to occasional natural mutations and variations that change one or a few amino acids; therefore, the proteins resulting from natural mutation are included in the invention, so long as the mutation does not destroy activity. An allelic mutation changing as many as 15 amino acids is not expected to destroy the activity of the lectin. Preferably, the allelic mutation would change no more than about 10 amino acids. Most preferably, only about five amino acids would be changed by an allelic mutation.

Also included within the invention are fragments of the lectins typified by that shown in FIG. 1. The fragments, in order to be included within the scope of the invention, must exhibit the specific properties characterizing the class, i.e., they must be soluble, capable of binding β-galactoside-containing moieties independent of the presence or absence of calcium ion, capable of stimulating hemagglutination of trypsinized rabbit erythrocytes in standard lectin assays which can be inhibited by lactose or thiogalactoside, and at least 90% homologous to the relevant portion of positions 2–135 of FIG. 1. While a specific minimum fragment length cannot now be identified, it is within ordinary routine experimentation to assay candidate fragments for these activities. It is well understood that only portions or fragments of a particular protein can have the activity of the complete natively produced protein. Deletion of one or several amino acids from either the N- or C-terminus generally does not destroy activity; in addition, internal regions not required to maintain conformation or associated with the active sites can be deleted. Whether or not a protein fragment falls within the scope of the invention is readily determined by means of the assay systems described below for determination of ability to effect hemagglutination both in the presence and absence of lactose or thiodigalactoside.

HL-60 cells and placenta tissue produce the preferred 14 kD β-gal binding lectin of the invention; this lectin is representative of the inventive class of 14-β-gal soluble lectins, one embodiment of which has at least one glycosylation site. As used herein, the phrase "14-β-gal mammalian lectin containing at least one glycosylation site" refers to a class of peptides having the characteristics of the group of lectins exemplified by the HL-60 lectin of FIG. 1 which contain at least one tripeptide sequence, Asn-X-Thr or Asn-X-Ser, which provides a glycosylation site.

To be included in the inventive class of 14-β-gal lectins or fragments containing at least one glycosylation site, a peptide must exhibit the following biological properties: For the forms which are not fragments, a molecular weight of the nonglycosylated protein is approximately 14 kD. As a practical matter, the molecular weight ranges from about 12–18 kD when it is measured by various techniques. The lectin or fragment is capable of binding β-D-galactoside containing moieties (e.g., lactose). Specifically, the inventive lectin causes hemagglutination of trypsinized rabbit erythrocytes in standard lectin assays, in which the stimulation of agglutination is inhibited by moieties containing the β-galactoside linkage, such as lactose and thiogalactoside. Hemagglutination can occur without a reducing agent, which is capable of maintaining thiol groups in the reduced form, but hemagglutination occurs without metal ions, in particular calcium ions.

The inventive lectins and fragments have at least 40% homology with the HL-60 lectin of FIG. 1, preferably at least 75% homology, more preferably over 90% homology and most preferably over 95% homology. The preferred location of the glycosylation site is at residues 96–99, as is the case for the lectin of FIG. 1. However, the glycosylation site can be within, at most, a four-amino acid spacing upstream or three-amino acid spacing downstream, i.e., between residues 92 and 101 inclusive. Other preferred locations include those which contain Asn, X (any amino acid), and Ser/Thr residues in any of the animal lectins at nonconserved regions.

The most preferred embodiment of the 14-β-gal lectins containing glycosylation sites is that of the HL-60 lectin of FIG. 1, particularly the lectin from HL-60 cell or placental tissue sources or a lectin from the naturally occurring mutants and allelic variants thereof.

Glycosylated forms of this unique lectin having a molecular weight in the range of approximately 12–18 kD are also within the scope of this invention. The glycosylation of these inventive lectins can be manipulated to provide different properties for therapeutic and diagnostic uses.

It is known, in general, that proteins exist in a variety of essentially equivalent forms including the acidic and basic salts thereof, forms which are derivatized at side-chain functional groups, forms associated with lipids and membranes, and other modifications made through post-translational processing of the cell expressing the DNA encoding the desired lectin. All of the proteins defined above are inclusive of these various forms.

Preparation of the Lectins and Fragments

The lectins of the invention can be isolated from native sources, synthesized, or produced by recombinant methods. The isolation of these lectins from native sources, such as HL-60 cells or placental cells, is described in detail in European Publication No. 337,799, published Oct. 18, 1989, and is incorporated herein by reference. This publication also describes the retrieval of cDNA encoding HL-60 lectin. The structure of the full length cDNA clone is shown herein in FIG. 1.

The lectins and fragments of the invention can be prepared, if desired, by standard solid phase or other peptide synthesis methods This mode of preparation is generally considered most suited for smaller peptide fragments. Although this method is clearly within the skill of the art with respect to the full-length lectin sequences, such as that shown in FIG. 1, part or all of the molecule can more conveniently be synthesized using recombinant techniques.

For recombinant production, the DNA which encodes the inventive lectin or fragment is mobilized by ligating the appropriate sequence to control sequences regulating expression, transfecting the resulting expression systems into appropriate hosts, and culturing the transformed or transfected hosts under conditions favorable for the expression of the DNA. For procaryotic systems, an intronless DNA is required; however, in eucaryotes a genomic DNA can also be used. Genomic DNA encoding the HL-60 and placental lectin and its naturally occurring mutants and allelic variants can be recovered from the HL-60 or placental genome using the cDNA of FIG. 1 as a probe.

The lectin-encoding sequence can be ligated into the expression system preceded by an ATG to obtain the lectin as a mature protein. Alternatively, signal sequences known to be operable in the intended host, such as the penicillinase or alkaline phosphatase system in bacteria, the alpha-factor system in yeast, or various hormone signal sequences in mammalian cells can be used to effect secretion by constructing the expression system with the DNA encoding signal in reading phase with the lectin DNA. The lectin could also be produced as a fusion protein by ligating the coding sequence into reading frame with an additional coding sequence if desired.

A variety of host systems with appropriate controls are by now well known in the art. For example, among procaryotic hosts, *E. coli* are preferred, although other bacterial strains, such as Bacillis and Pseudomonas, could be used. Suitable control systems include, but are not limited to, promoters associated with bacterial proteins such as β-lactamase and lactose (lac) promoter systems (Chang et al., *Nature* (1977) 198:1056; the tryptophan (trp) promoter system (Goeddel et al., *Nucleic Acids Res.* (1980) 8:4057); and the lambda-derived $P^L$ promoter and N-gene ribosome binding site system (Shimatake et al., *Nature* (1981) 292:128).

Similarly, a variety of vectors and promoters is known for yeast systems and includes, but is not limited to, the promoter for 3-phosphoglycerate kinase (Hitzeman et al., *J. Biol. Chem.* (1980) 255:2073), the enolase gene promoter (Holland, M. J., et al., *J. Biol. Chem.* (1981) 256:1385), and the leu2 gene obtained from YEp 13 (Broach, J., et al., *Gene* (1978) 8:121).

For expression in cells of higher organisms, promoters operable in such cells include, but are not limited to, viral promoters such as the SV40 promoter (Fiers et al., *Nature* (1978) 273:113) and promoters derived from adenovirus, bovine papilloma virus, Rous sarcoma virus, and so forth. Also usable are regulatable promoters such as the metallothionein I or metallothionein II promoters. Control sequences for retroregulation are also available such as that associated with the crystal protein gene of *Bacillus thuringiensis*.

Currently available also are systems for production of recombinant proteins in insect cells and in plant cells, although plant cell systems are currently less convenient. Their inconvenience, however, is a result of the current state of the art, and not of an inherent incompatibility between this host cell system and the gene encoding the proteins of the invention.

The appropriate coding sequences are ligated to the control sequences in operable configuration and in suitable vectors for transfection into the intended host. The vectors include, but are not limited to, plasmids, virus particles and phages depending on the intended host and the mode of transformation. "Transformation", as used herein, includes all forms of causing uptake of foreign DNA by a host cell including viral infection, transduction, conjugation or, probably most common, induction of uptake in vitro by transfection using transfecting agents such as calcium chloride or DEAE/dextran, depending on the host.

The transformed cells are then screened for those which contain the desired DNA and the successful transformants are cultured under conditions which affect the expression of the coding sequences. The lectin produced is then purified from the medium (if the construction results in secretion) or from the lysed cells (if the construction results in an intracellular protein).

Whether the lectin is isolated from natural sources, synthesized, or produced by recombinant methods, the lectin can be purified by standard methods, including extraction in lactose solution followed by chromatographic procedures. Convenient chromatographic procedures includes chromatography on lactose sepharose gels, a sephadex S-200 HR column, or a lactose-HEMA column. After using any of these chromatography procedures, the presence of the protein in the active fractions can be easily detected by the ability of the fraction, after removal of the lactose, to cause hemagglutination of trypsinized rabbit erythrocytes, wherein the hemagglutination is inhibited by millimolar concentrations of lactose or thiodigalactoside.

Antibodies Reactive with the Inventive Lectins

The lectins of the invention can be used in conventional ways to raise antisera reactive with, and specific for, these lectins. An antibody "specific for" the referenced lectin means an antibody which is immunoreactive with this lectin or, in some cases, with other lectins of the invention, but not immunoreactive with non-galactose binding lectins. Because of the extensive homology of the FIG. 1 HL-60 lectin with other lectins of the inventive class, polyclonal antibodies raised against this lectin are likely to cross-react with other inventive lectins. However, by producing monoclonal antibodies with respect to this lectin, antibodies specific to one particular embodiment or to a selected group of inventive lectins can be generated. In addition, antibodies specific for various glycosylated forms can also be prepared.

Antibodies can be prepared using known techniques with specificities for any particular member of the inventive 14-β-gal lectin class, including those with at least one glycosylation site and in nonglycosylated and especially glycosylated forms.

In short, the antibodies within the scope of the invention are those which are reactive with one or more members of the lectins of the invention, but the antibodies are not cross-reactive with the lectins presently known in the art. Also included in the scope of the invention are antisera raised by any of the lectins of the invention, since these antisera are unique to these lectins even if they contain antibodies which are cross-reactive in some measure with known lectins.

Uses of the Inventive Lectins

The lectins and fragments of the invention and their compositions are useful in a range of therapeutic and diagnostic applications. In general, these peptides and proteins are particularly useful as immunosuppressants. The inventive lectins and fragments can be used in the treatment of autoimmune diseases such as myasthenia gravis. Other autoimmune diseases which are subject to treatment by these lectins include rheumatoid arthritis, systemic lupus erythematosus, juvenile diabetes, and multiple sclerosis. The inventive lectins can also be useful in controlling allergic reactions.

Since these proteins are immune system regulators, they are also useful in the prevention of graft-versus-host disease and inhibition of rejection of transplants in general. Thus, the inventive lectins and fragments can be administered in conjunction with various surgical transplantations including skin allografts, bone marrow transplants, and organ transplants such as kidney, heart, liver or lung transplants. When used as an immunosuppressant, either in treating autoimmune conditions or in preventing transplant rejection, the lectins and fragments of the present invention can be administered along with amounts of known general immunosuppressants that enhance their effects. Such suitable general immunosuppressants include, for example, cyclophosphamide, prednisone, cyclosporin, rapamycin, other macrolide derivatives such as FK506, azathioprine, mycophenolic acid, anti-Tac, lymphocyte immune globulin, and OKT3 antibodies. The inventive lectins and fragments thereof can be administered simultaneously or sequentially with general immunosuppressants.

The inventive lectins are also useful in drug delivery and diagnostic applications by carrying the chemical entity to suitable targets. Suitable targets for lectins are those cells of mammalian subjects with galactose-terminating ligands. These lectins are coupled to a drug, for example, cytotoxic or therapeutic agents, or to a label, by methods in the art. Okuda et al., *Infect. Immun.* (1980) 27:690–92; Samoszuk et al., *Antibody Immunoconjugates Radiopharm.* (1989) 2:37–46; and Knowles et al., *J. Clin. Invest.* (1973) 52: 1443–52. In addition, antibodies specific for the inventive lectins are useful in targeting drugs or labels to tumors, since the level of certain lectins increases on the cell surface in metastatic cancer. Anti-lectin antibodies are coupled to the drug, for example, a cytotoxic or therapeutic agent, or label. For diagnostic purposes, the label coupled to the lectin or anti-lectin can be administered to a living mammalian subjects (in vivo use) or used in in vitro tests, for example, as part of a test kit.

While not wishing to be bound by any theory, the Inventors propose that the inventive lectins behave as immunomodulating agents and regulate the immune system by binding activated lymphocytes to other activated lymphocytes and to endothelial cells, for example on the inside of blood vessels. Surface glycoproteins on resting lymphocytes contain terminal sialic acid residues, but activated lymphocyte glycoproteins are desialylated to expose galactose. Hence the inventive lectin is specific for activated T-cells and causes them to agglutinate or to adhere to endothelial cells. It is believed that these interactions may inhibit or modify T-cell migration, e.g. extravasation from the circulation, during inflammation.

The inventive lectin may affect the immune response by another route. Antibodies specific for the inventive lectin have been observed reacting with human thymic tissue, particularly thymic cortical epithelial cells whose interaction with immature cortical thymocytes is crucial in deleting auto-reactive T-cells. Although the thymus typically atrophies early in life and is not known to play an active role in adult autoimmune pathology, administration of the inventive lectin may possibly increase thymic deletion of autoreactive T-cells.

Formulation

For use in therapeutic applications, the lectins and fragments are formulated in a manner suitable for the desired mode of administration using formulation technology known in the art as described, for example, in *Remington's Pharmaceutical Sciences*, 17th edition, Mack Publishing Co., Philadelphia, Pa. Typical formulations for injection include admixture with physiological buffer for injection such as Hank's solution or Ringer's solution, encapsulation in liposomes or other emulsifying agents suited for drug delivery, and the like.

A particularly preferred method of formulation provides for long term storage of the soluble lectin of this invention in the lyophilized, or freeze-dried, form. Lyophilization is preferably conducted in the presence of a concentration of a carbohydrate which is effective to stabilize the lectin during the lyophilization process and at a relatively low pH of about 5. This pH appears to minimize oxidation. Also preferred is addition of a low ionic strength buffer. Suitable protective carbohydrates include, but are not limited to, monosaccharides such as galactose; disaccharides such as lactose, maltose and sucrose; and oligosaccharides containing galactose moieties. The preferred carbohydrates are lactose and maltose. The most preferred protective carbohydrate is lactose. Because the lyophilized product is used in a pharmaceutical composition, the protective carbohydrate must be physiologically and pharmaceutically acceptable at the concentrations used. The effective concentration of the protective carbohydrate can be 1–40% wt./volume but is preferably around 5–15%, and even more preferably around 10%.

The maintenance of the pH at about 4 to 8, preferably at about 4.5 to 6, and more preferably at about 5 discourages oxidation of cysteine residues. It is further preferable to maintain this pH in a buffer of relatively low ionic strength, since the freezing point of the mixture is then not lowered significantly. Preferably, the buffer is bicarbonate, gluconate, lactate, acetate or phosphate. Most preferably, the buffer is citrate. It is preferred that the buffer concentration be about 5–20 mM, more preferably 7–12 mM, and most preferably about 10 mM. Other conditions of lyophilization can also be used; however, it has been found that the presence of about 10% lactose in about 10 mM citrate and a pH of 5 are particularly favorable conditions.

Administration and Dosage

The dosage level and manner of administration of the lectins and fragments of the invention depends on the indication and the subject, as well as the severity of the condition to be treated. When the full lectin is administered, a higher dose (mg/day) is required than when active fragments of the lectin are administered. Some indications for use (such as transplantation rejection, particularly full-blown rejections) require higher doses than to others (such as rheumatoid arthritis, particularly between flare-ups of the disease).

The subject who receives the inventive lectin can be a mammal, bird or other vertebrate, because the lectins of mammals, birds, eels, and fish have been found to be related. For purposes of this invention, the term subjects refers to mammalian subjects, including humans, farm animals, sport animals and pets. Farm animals include, but are not limited to, cows, hogs and sheep. Sport animals include, but are not limited to, dogs and horses. The category pets includes, but is not limited to, cats and dogs. Smaller animals generally require somewhat higher doses per kilogram.

Preferred dose levels range from about 0.004 mg/kg/day to about 2 mg/kg/day. When the inventive lectins are used in conjunction with general immunosuppressants, however, lower dosages are generally preferred.

In general, the inventive lectins or fragments are administered in a manner suitable for peptides or proteins—i.e., by injection or by other parenteral routes including transmembrane or transmucosal transitions. Formulations suitable for these modes of administration are well understood in the art. Oral administration is always desirable, provided the formulation permits the substantially intact lectin or fragment thereof to survive the digestive tract and enter the bloodstream.

The following examples are intended to illustrate but not to limit the invention.

EXAMPLE 1

Preparation of the Pharmaceutical Composition

The European publication 337,799, published Oct. 18, 1989, cited above, describes in detail the isolation of 14 kD lectin from HL-60 cells or placenta and the recombinant production of HL-60 lectin in mammalian and bacterial cells. In the examples described hereinbelow, the lectin was prepared recombinantly in *E. coli* substantially as described in the above-referenced application, and as further described by Couraud, P. O. et al., *J. Biol. Chem.* (1988) 264:1310–1316, also hereby incorporated herein by reference.

Briefly, *E. coli* containing an expression plasmid in which the DNA to be expressed is that shown in FIG. 1, were grown in Luria broth (LB) to stationary phase. In general, about 5 g of cells wet weight per liter of broth were typically obtained. The cells were then frozen and the lectin was extracted by purification procedures.

The frozen cell samples were thawed in ice overnight or under cool running water to expedite the thawing. The cells were collected in a beaker and slowly mixed with a 15 mM β-mercaptoethanol (B-ME) buffer to form a thin paste having a density of approximately 0.1 to 0.3 g/ml. The buffer was a solution comprised of 0.02M Tris, 0.15M NaCl, 0.002M EDTA, and 15 mM Mercaptoethanol having of pH of 7.5. The cells and buffer were maintained in a cold environment. Preferably, the cold environment is a room that is maintained between 2 and 6° C. The cells and buffer were mixed for a time period as long as two hours until a homogeneous, lump-free, cell suspension results. Magnetic mixers, overhead mixers or other well known mixers or other mechanical disruption devices could be used. However, the overhead mixer has been most effective for mixing large amounts of cells.

The cell suspension was passed twice through a high pressure Microfluidics homogenizer, operated at 15,000 psi. The homogenizer was packed in ice to prevent heating of the cell suspension. Tris buffered saline (TBS) was used to recover the disrupted cell product obtained from the homogenizer. The disrupted cells were next placed in an RC5B centrifuge (DuPont de Nemours, Wilmington, Del.) at the maximum speed (approximately 8000 rpm) for thirty minutes to separate cell debris. The centrifuged cell product was next decanted to separate the protein supernate from the cell pellets. The supernate contains the desired lectin. However, the cell pellets can be quick frozen on dry ice for later possible application.

The supernate was mixed with an aqueous solution containing 10% by volume, pH 8.0, polyethylenimide (PEI). The supernate/PEI mixture was stirred slowly in a cold environment for approximately one half hour. A milky white precipitate formed which contains the desired nucleic acids. The mixture containing the precipitate was next placed in the centrifuge at the maximum speed (approximately 8000 rpm) for 20 to 30 minutes to remove the precipitated nucleic acids. A clear yellow/tan supernate was obtained from this second centrifugation process. The yellow/tan supernate can be stored at 4° C. overnight before processing it through chromatography columns the next day.

In an alternative method, PEI can be added before the first centrifugation step, instead of before the second centrifugation step, which can then be skipped. However, the addition of PEI before the second centrifugation step is preferred because it preserves the cell pellets without the added protein of the PEI precipitate. Furthermore, testing revealed that no loss of product resulted by adding the PEI before the second centrifugation step. However, since the second centrifugation step adds at least one additional hour to the total process time, an alternative method of adding PEI before the first centrifugation step can be used to make this claimed invention in less time.

The next step was chromatography on lactose Sepharose gels. First, the lactose Sepharose column (Pharmacia, Uppsala, Sweden) was equilibrated with TBS and MCE buffer. Next, the yellow/tan supernate was loaded onto the column at 12 to 20 cm/hr. Then, the column was washed with equilibrium buffer at 20 to 25 cm/hr until UV absorbance returned to baseline. Next, the column flow was reversed, and the buffer wash was continued for a time period equal to the time it would take to fill one-half of the column at the desired flow rate. The product was then eluted with 0.1M lactose in gradient form. The gradient method of elution is preferred for smaller quantities; however, the batch method is preferred for larger quantities.

An alternative chromatographic procedure involves ion-exchange chromatography on a Sephadex S-200 column (Pharmacia). The column is depyrogenated using sodium hydroxide washes of decreasing concentration. The S-200 column is next equilibrated with 10 mM citrate, having a pH of 5.0. The yellow/tan supernate is loaded onto the column at a rate of approximately 15 cm/hr. The supernate can be loaded at a rate up to 6% by volume of the total solvent exchange. The product concentration at loading should be as high as possible to eliminate or minimize the need to further concentrate the eluted product. Immediately upon obtaining the peak from the S-200 column, the eluted product is diluted in a 1:1 ratio with sterile-filtered 10% Lactose in 10 mM Citrate having a pH of 5.0.

A further alternative chromatographic procedure includes the use of a Lactose-HEMA column.

The eluted product obtained from the above chromatographic procedure was stored in small vials, with about 1 to 5 ml of the product in the appropriately sized vial. The vials were sterilized prior to filling by heating the vials to about 150° C. for a minimum of 4 hours. Any leak tight caps, such as grey split stoppers, can be used to contain the product within the vial.

The product was next lyophilized using a Virtis lyophilization chamber or unit. The vials containing the product were placed in the unit's chamber and frozen to −30° C. This temperature was maintained for at least 3 hours. A vacuum was applied to the chamber and the pressure was reduced to less than about 100 torr and preferably about 15 torr. The Virtis unit was maintained at −30° C. and 15 torr for at least two hours. After the freezing stage, the unit and vials were brought to 0° C. and maintained at this temperature for at least two hours. The temperature was further increased to 30° C. in 5° C. increments over a six hour period. Once the 30° C. temperature was reached, the unit was maintained at 30° C. for at least two more hours. The vials were then sealed under vacuum with stoppers and aluminum seals, over which vial caps were crimped.

The recombinantly produced and purified lectin described above was tested to assure that it has the same electrophoretic and chromatographic mobility, the same N-terminal amino acid sequence, and the same immunoreactivity on Western blots as that of the 14 kD inventive lectin derived from either human placenta or HL-60 cells.

EXAMPLE 2

Effect of the Inventive 14 kD Lectin on Lymphocyte Binding to Endothelial Cells

To analyze the mechanism of action of the inventive lectins as immunomodulators, a test was devised to discover whether these lectins bind lymphocytes and/or T-cells to endothelial cells. Thin sections of tissue containing inflamed rat brain vascular endothelium were prepared. Rat lymph node lymphocytes and human T-cells of the Jurkat line ($10^7$/ml in Dulbecco's modified Eagle medium (MEM) with 5% fetal bovine serum (FBS)) were treated with 250 µg/ml of the lectin of Example 1, with the lectin plus 1 mM lactose, or with no additions and subsequently were placed on ice for 30 min. The lectin severely agglutinated the T-cells and moderately clumped the rat lymphocytes. These effects were not observed when lactose was added or when there were no additions.

Next the treated cells were layered onto the vascular endothelial sections. These treated sections were gyrated (60 rpm) on ice for 30 min. Then the sections were fixed, washed and stained with toluidine blue for viewing. Both the rat lymphocytes and the T-cells bound to the endothelium of inflamed cerebral blood vessels. T-cells treated with lectin did not bind to the endothelium, possibly because the T-cells were agglutinated and unavailable to react. Lectin strongly accentuated the binding of rat lymphocytes to the endothelium. Excess lactose eliminated the lectin effect both on T-cells and lymphocytes, so that binding was the same as the no-lectin control. Table 1 summarizes these results:

TABLE 1

| | Binding to Inflamed Brain Endothelium | | |
|---|---|---|---|
| | Control | Lectin | Lectin + Lactose |
| Rat lymphocytes | + | ++++ | + |
| Jurkat T-cells | ++++ | +/− | ++++ |

While not wishing to be bound by any particular theory, it appears that lectin enhances binding of rat lymphocytes to vascular endothelium by reacting with both the endothelium and with the lymphocytes and serving as a molecular bridge. The lectin did not similarly bind T-cells to endothelium, possibly because the T-cells were so thoroughly agglutinated that no free cells were available to bind the endothelium.

Sections of lymphoid organs (lymph nodes and Peyer's patch) were tested as above. Lectin had no noticeable effect on rat lymphocytes; however, because control level binding was very low, this result cannot be relied on.

EXAMPLE 3

Cross-Reactivity of a 14 kD Lectin With Endogenous Lectin

Figure 2B:
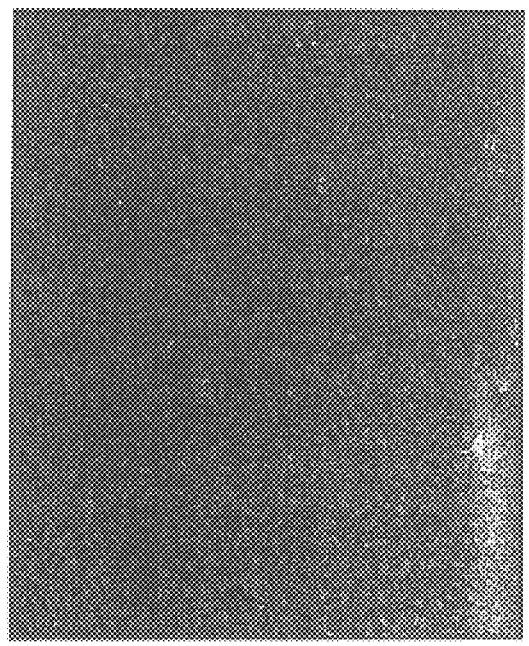

In further characterizing the effects of the inventive lectin on the immune response, a test was devised to determine whether the inventive lectin is normally present in lymph nodes where it could affect thymic maturation. First, anti-lectin antiserum was prepared by injecting the inventive recombinant lectin into rabbits. Polyclonal antiserum specific for the inventive lectin was obtained from the immunized rabbits. Slides were made of sections of human thymic cortex and of cultured thymic epithelial cells. These sections of human thymic tissue and cultured thymic epithelial cells were incubated with the rabbit anti-lectin antisera. The cross-reactivity was detected at a dilution of 1:1000 by labeling the antibody-coated sections with goat anti-rabbit horseradish peroxidase and adding substrate. The thymic sections were examined by microscopy and had highly stained thymic cortical epithelial cells. The cultured thymic epithelial cells were also highly stained. The epithelial nature of the stained thymic cells was confirmed by counterstaining with cytokeratin antibodies which are specific for epithelial cells. See FIG. 2 for the comparison of anti-lectin staining and anti-cytokeratin staining. Thus, a protein which is immunologically cross-reactive with the inventive recombinant lectin has been localized to epithelial cells in human thymic tissue. In addition, protein extracts of cultured thymic epithelial cells stained positively with the rabbit-polyclonal antiserum on Western blots in an immunoreactive band which comigrated with the inventive lectin.

Figure 3:
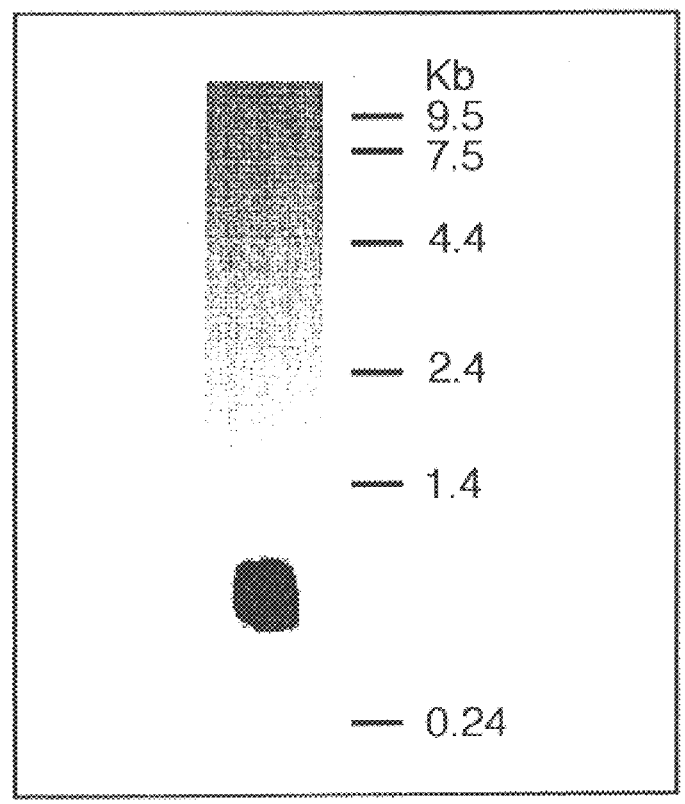
FIG. 3 shows an electrophoresis gel with staining in a location indicative of mRNA for the inventive lectin in thymic epithelial cells.

The cDNA for the inventive lectin was used as a hybridization probe against thymic epithelial cell RNA. A discrete transcript was detected and had the correct corresponding size, as shown in the representation of the electrophoresis gel in FIG. 3. Thus, it appears that thymic cortical epithelial cells have a protein with a molecular weight, antigen reactivity and DNA sequence similar to those properties of the inventive lectin.

Because interaction between thymic epithelial cells and immature cortical thymocytes is crucial for proper selection of immunocompetent T-cells, the inventive lectin appears to affect thymocyte maturation. In addition, in comparison to mature T-cells, immature cortical thymocytes show much higher levels of the galactose ligand which is recognized by the inventive lectin. This further supports interaction of the inventive lectin with immature thymic cells, rather than an effect on mature T-cells.

Furthermore, galactose-terminating ligands are present on the cell surfaces of migrating leukocytes and could be responsible for leukocyte recognition by lectin-containing homing receptors. Because the inventive lectins are specific for galactose ligands, the inventive lectins should affect the extravasation caused by leukocyte-receptor interaction. This can also be conveniently tested.

Figure 4:
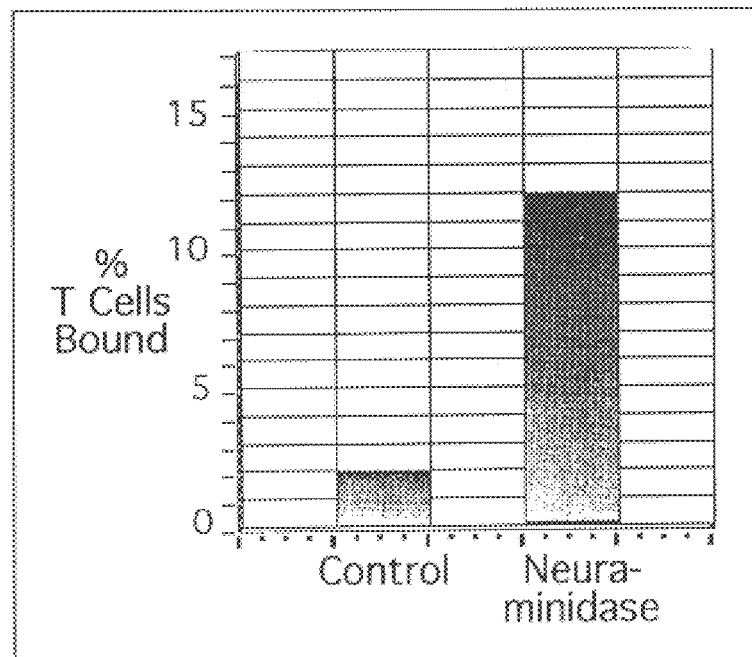
FIG. 4 shows the percentage of ARR T-cells that adhered to thymic epithelial cells with and without enzyme treatment.

The effects of the lectin on the binding of cultured T-cells to thymic epithelial cells were further tested according to the protocol of Singer et al. (*Proc. Natl. Acad. Sci.* (1986) 83:6588–92). T-cell lines MOLT4 and ARR (a T-cell line with sialic-acid-terminating glycoproteins) were incubated with tritiated thymidine. Next, the cells were treated with neuraminidase (which cleaves terminal sialic acids from the glycoproteins on ARR cells and leaves terminal galactose), galactosidase, endolactosaminidase or no enzyme. After this step, the cells were incubated with and without lectin. All the treatment and control groups of T-cells were layered over thymic epithelial cells, incubated and washed as described in Singer et al. Lastly, the amount of bound T-cells was quantitated by decompositions per minute (DPM). Only lectin-treated T-cells with terminal galactose residues appreciably bound to thymic epithelial cells, as shown in FIG. 4.

EXAMPLE 4

Assay for β-galactoside Binding Activity of Lectins

Figure 5:
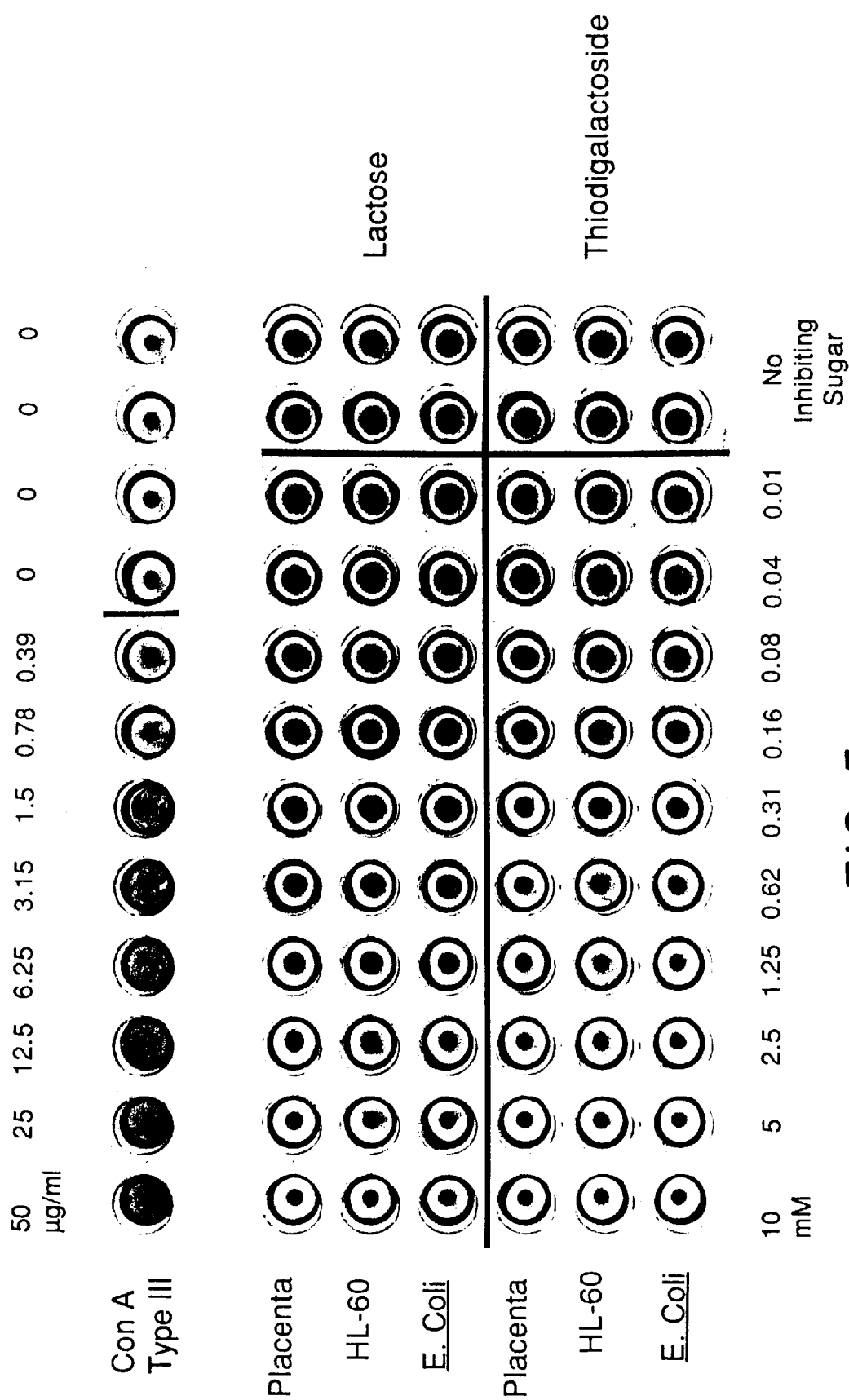
FIG. 5 shows results of hemagglutinin bioassay of purified lectins from human placenta, HL-60 cells and $E.$ $coli$ cells transfected with vectors containing lectin cDNA and an operably linked secretion signal, and inhibition of agglutination by sugars.
Figure 6:
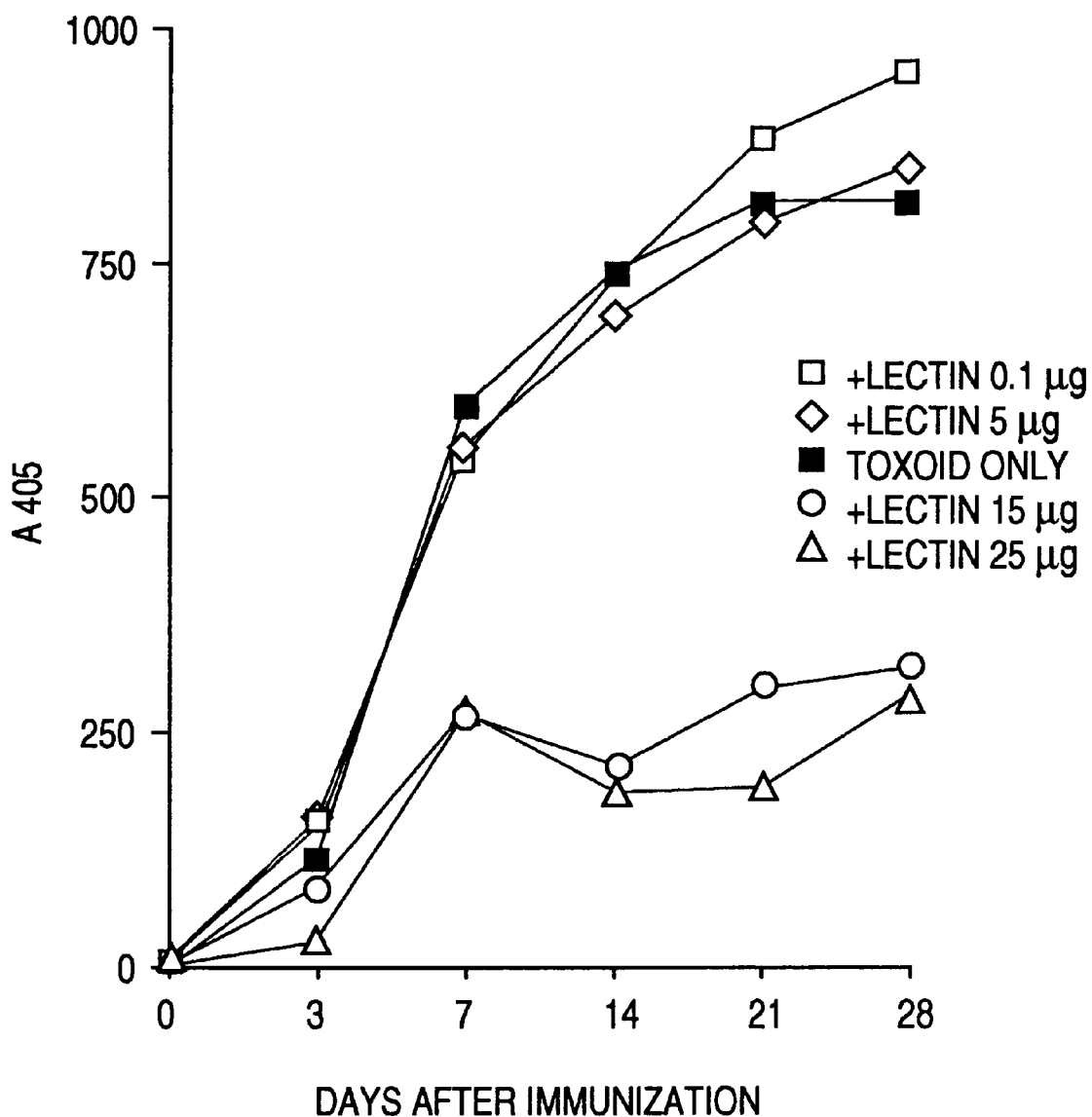
FIG. 6 shows the effect of several doses of the inventive lectin on the primary immune response to tetanus toxoid.
Figure 7:
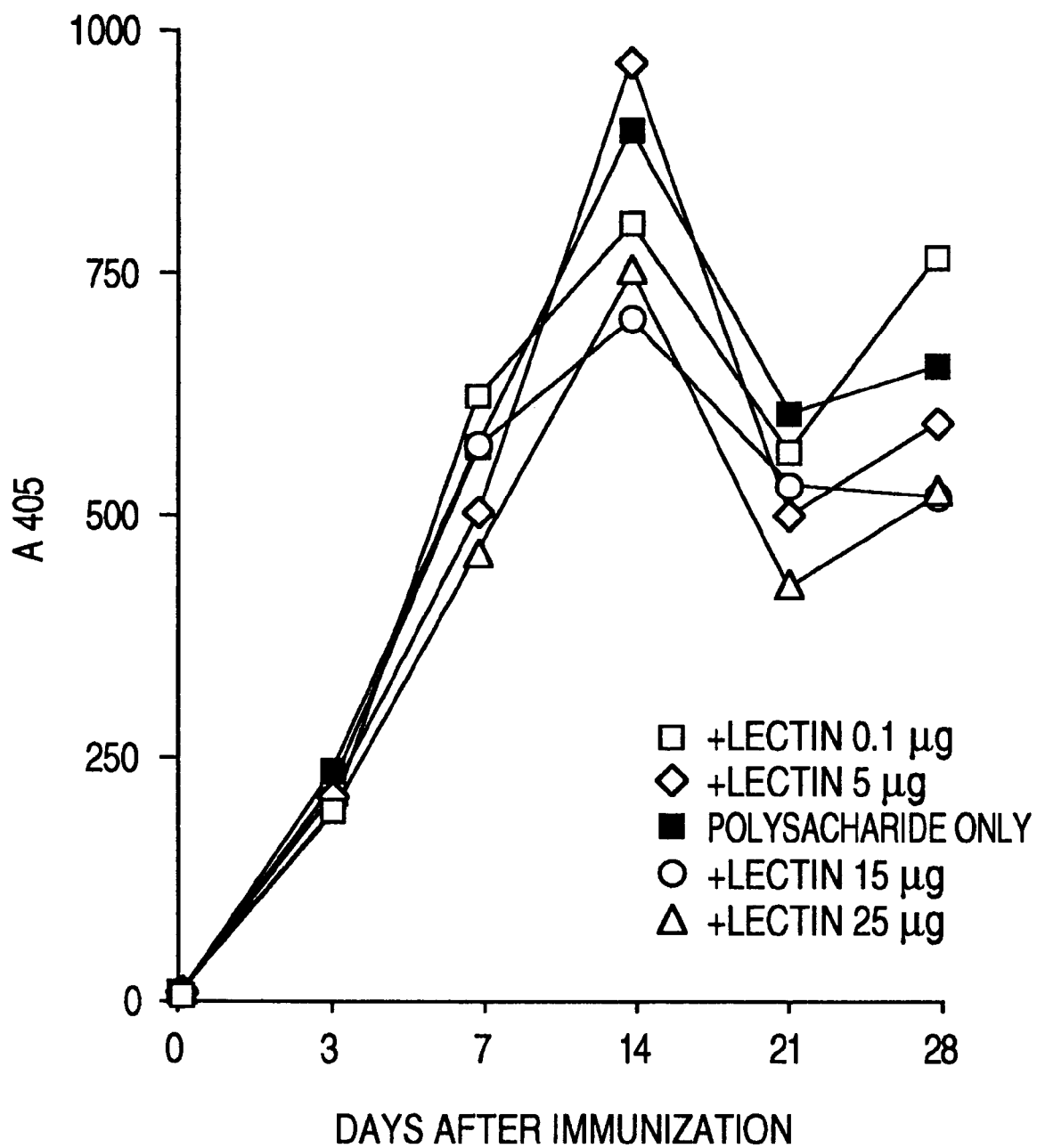
FIG. 7 shows the effect of several doses of the inventive lectin on the primary immune response to pneumococcal polysaccharide.
Figure 8:
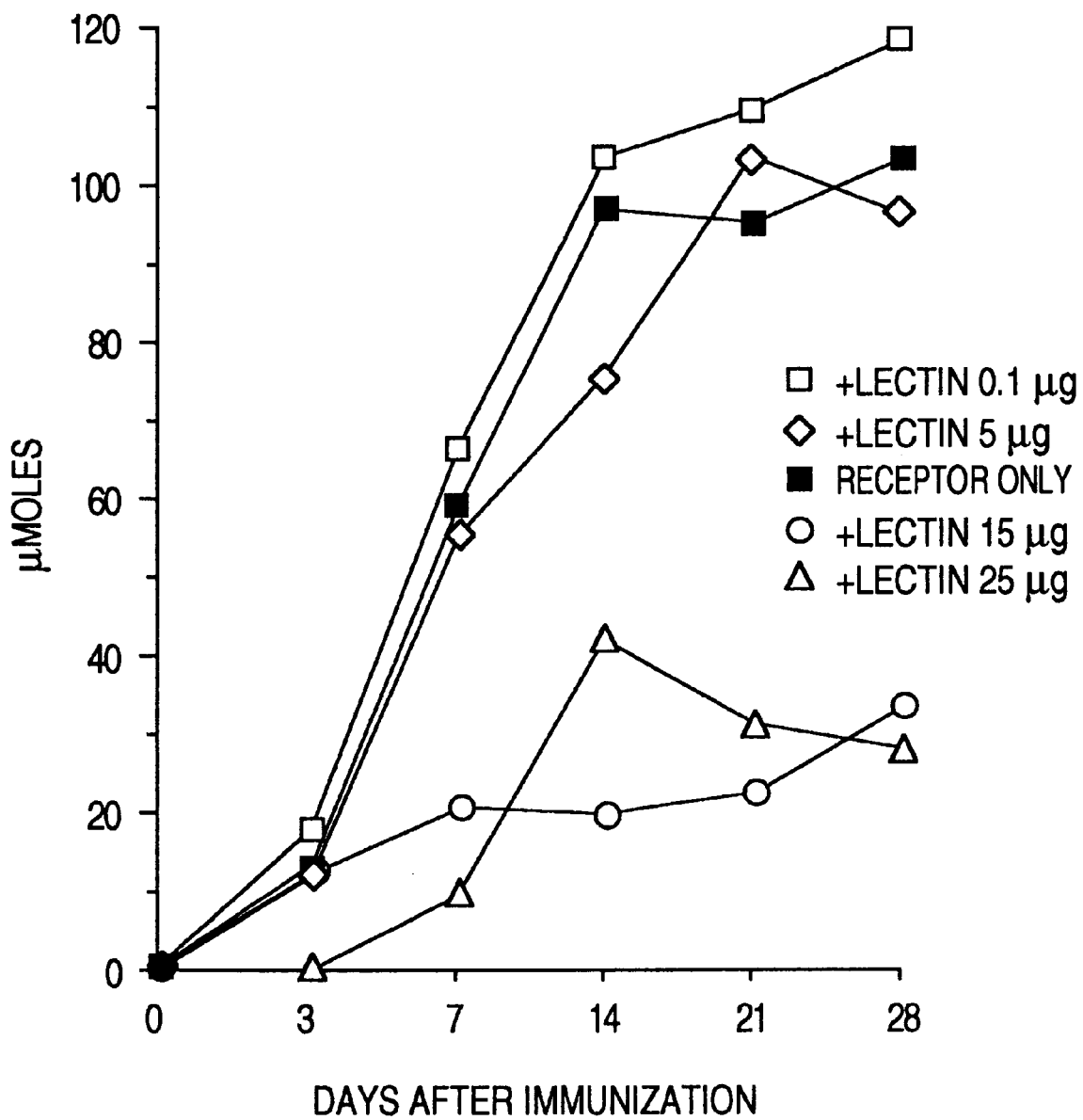
FIG. 8 shows the effect of several doses of the inventive lectin on the primary immune response against the Torpedo receptor.
Figure 9:
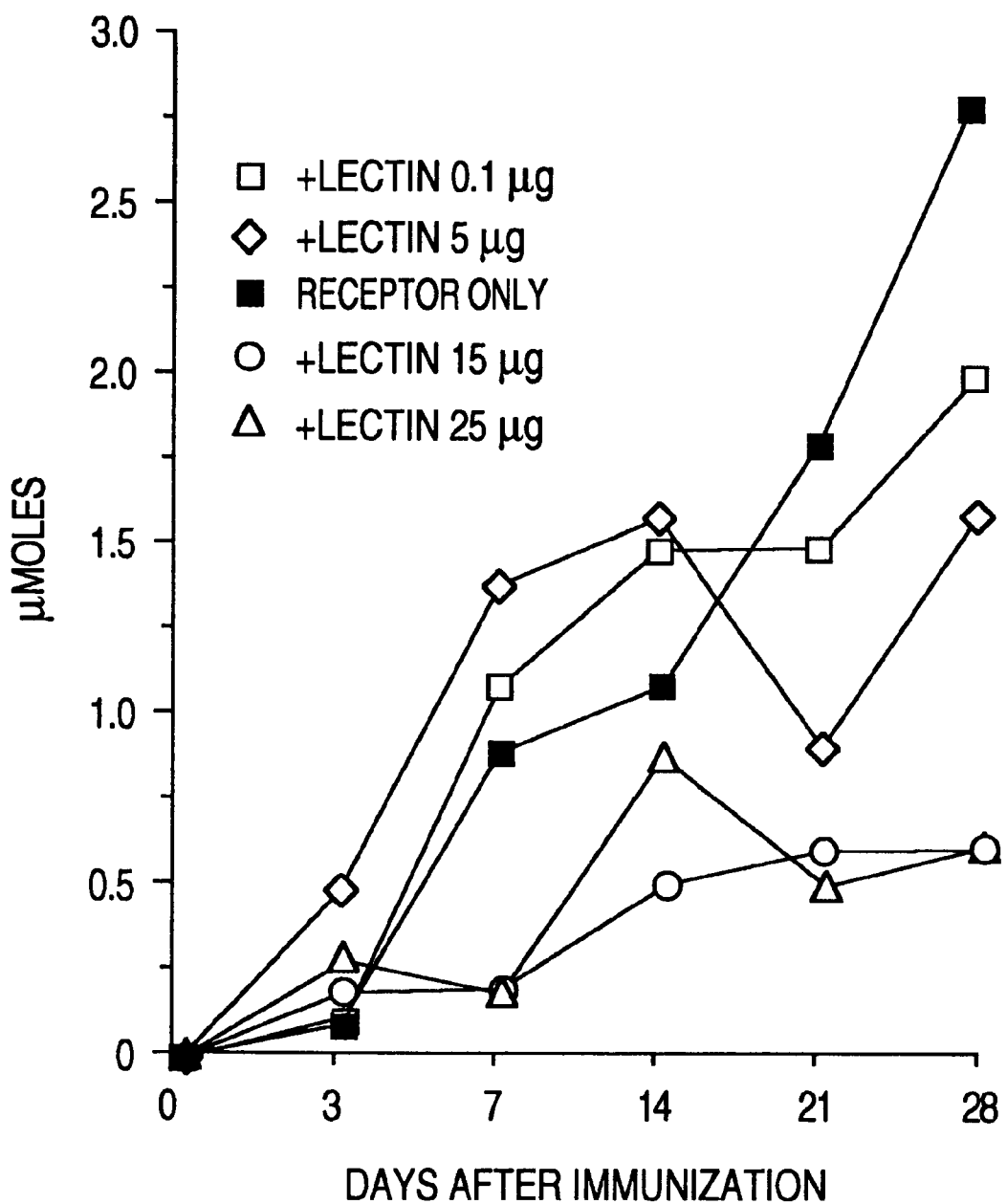
FIG. 9 shows the effect of several doses of the inventive lectin on the primary immune response against mouse skeletal muscle receptor in animals immunized with the Torpedo receptor.

Biological activity of the inventive 14 kD lectins 1) isolated from HL-60 cells, 2) isolated from placenta tissue or 3) prepared recombinantly from *E. coli* cells transfected with lectin cDNA operably linked to a secretion signal was ascertained by agglutination of trypsinized rabbit erythrocytes. As seen in FIG. 5, the top row shows a Concanavalin A control with an agglutination end-point at 1.5 μg/ml. The lower six rows show the three purified inventive 14 kD lectins incubated with varying concentrations of completing sugars, β-lactose and thiodigalactoside, which are known to be potent inhibitors of the 14 kD placental lectin. Thiodigalactoside inhibited agglutination of the erythrocytes at concentrations greater than 0.31 mM and β-lactose inhibited agglutination at concentrations greater than 1.25 mM.

EXAMPLE 5

Effect of 14 kD β-gal Lectin in a Myasthenia Gravis Model

Experimental autoimmune myasthenia gravis (EAMG) is an antibody-mediated autoimmune disease responding to acetylcholine receptors (AChR). This condition in mice is a recognized model for studying the effects of the autoimmune response on neuromuscular transmission (Levi, G. et al., *Eur. J. Immunol.* (1983) 13:500–507; Lefvert, A. K. et al., *Scand. J. Immunol.* (1978) 8:525; Lefvert, A. K. et al., *J. Neuro. Immunol.* (1985) 9:41; Lefvert, A. K. et al., *Eur. J. Immunol.* (1982) 12:790). It appears that myasthenia gravis is mediated by T helper cells, which produce acetylcholine receptor antibodies. The disease is induced in mice by injection of acetylcholine receptor. The acetylcholine receptor is obtained from the electric organ of the ray *Torpedo marmorata* and purified by affinity chromatography on Naja naja siamensis neurotoxin crosslinked to Sephadex.

Young adult female BALB/c and C57B/6 mice (2–4 months of age) were used because they differ in EAMG susceptibility. The mice were injected subcutaneously with 10 μg of purified acetylcholine receptor, in Freund's complete adjuvant without and with the 14 kD-β-gal lectin.

Blood was obtained after 3 days and after 1, 2, 3 and 4 weeks. To follow the development of the disease, the mice were observed daily for signs of neuromuscular dysfunction and after 10 days subjected to forced exercise using repetitive grasping, swimming and inverted hang. These exercises were repeated after warming under a heat lamp at 35° C. for 5 min. The results of these observations are presented in Table 2 and show that in both strains of mice tested at higher lectin dose levels, the recombinant lectin markedly slowed neuromuscular deterioration.

TABLE 2

| Mouse Strain | Mice Showing Clinical Signs of Neuromuscular Dysfunction (%) | |
| --- | --- | --- |
| | BALB/c | C57B/6 |
| Receptor Only | 25 | 68 |
| Receptor + 2.5 μg Lectin | 18 | 59 |
| Receptor + 12 μg Lectin | 4 | 11 |

After the observation period, the animals were sacrificed, skinned, and eviscerated; and a cholinergic receptor (AChR) extract was prepared as described by Lefvert, A. K. et al., *Scand. J. Immunol.* supra for determination of total AChR content and Ig-complexed AChR content, as described therein.

Briefly, to determine total AChR content, known portions of the AChR extracts were incubated with a ten-fold excess of $^{125}$I-alpha-bungarotoxin for 1 hour at 37° C. so as to label the receptor for quantitation. The mixture was subjected to gel filtration on Sephacryl G200 to separate free and bound toxin. To determine the amount of AChR complexed to IgG or IgM antibodies, the extract was incubated with a ten-fold excess of labeled bungarotoxin overnight at 4° C.; anti-mouse IgG or IgM was then added and the samples incubated overnight at 4° C., followed by separation of the precipitates, washing and counting.

The results are shown in Table 3 together with the amount of recombinant lectin coadministered. These data show that single subcutaneous doses of about 7.5–12 µg recombinant lectin lowered both AChR loss and the amount of Ig-complexed AChR.

TABLE 3

Muscle Acetylcholine Receptor (AChR) Content in Mice Immunized with AChR With and Without Lectin (Determinations Made 10 Days After Injection)

| | Carcass AChR Content (mol × $10^{-11}$) | % of AChR Complexed with Ig |
|---|---|---|
| Normal mice | 3.9 ± 0.7 | 0 |
| AChR + lectin (0.1 µg) | 0.8 ± 0.4 | 48 ± 6.0 |
| AChR + lectin (1 µg) | 1.4 ± 0.3 | 52 ± 2.0 |
| AChR + lectin (5 µg) | 0.9 ± 0.5 | 44 ± 5.0 |
| AChR + lectin (15 µg) | 3.5 ± 0.4 | 11 ± 10.7 |
| AChR + lectin (25 µg) | 3.2 ± 0.6 | 11 ± 7.8 |
| AChR only | 1.5 ± 0.2 | 65 ± 2.6 |

EXAMPLE 6

B-Cell Repertoire of Mice Immunized with the Acetylcholine Receptor, Tetanus Toxoid or Pneumococcal Polysaccharide The effect of the recombinant lectin on B-cell activation in BALB/c mice was also assayed using standard assays determining the number of hybridomas secreting antibodies to the administered antigen.

Three BALB/c female mice (7–8 weeks old) were injected intraperitoneally with 5 µg of AChR antibody, tetanus toxoid or pneumococcal polysaccharide, respectively, in complete Freund's adjuvant. Two weeks later, the mice were injected intravenously with the same amount of antigen in 0.15 M sodium phosphate buffer, pH 7.4. Tetanus toxoid was obtained from the Swedish National Bacteriological Laboratory and consisted of formalin-treated tetanus toxin (normally used for vaccination). A mixture of capsular polysaccharide extracts from 23 different serotypes of *Streptococcus pneumoniae* (Pneumovax®) was obtained from Merck Sharp & Dohme, Inc. (West Point, Pa.). Three other mice of the same strain were similarly immunized with these antigens in combination with 15 µg of the recombinant lectin; controls received only the antigens.

The animals were sacrificed 4 days after the booster injection and spleen cells ($10^8$ cells) were fused with the nonsecreting B-lymphocytoma cell line SP2-OAg14 ($2 \times 10^7$ cells). The cell mixture was distributed in 6×96 Costar tray wells ($2 \times 10^5$ cells/well) with a feeder layer of mouse peritoneal macrophages ($5 \times 10^5$ cells/well). From the third day in culture HAT (hypoxanthine-aminopterin-thymidine) medium was added. After 10–14 days, supernatants were assayed for binding to the respective antigens used for immunization using an enzyme-linked immunosorbent assay (ELISA).

The results in Table 4 show that coadministration of lectin is effective in reducing the number of primary clones producing antibodies against AChR and tetanus toxoid. Coadministration of lectin reduced only slightly the number of hybridomas producing antibodies immunoreactive with the polysaccharide. It is believed that the B-cell response to the AChR and tetanus toxoid antigens is T-cell dependent, while that to the polysaccharide is independent of T-cells.

TABLE 4

Number of Clones Producing Antibodies Against Torpedo Receptor, Tetanus Toxoid and Pneumococcal Polysaccharide (180 Primary Clones for Each Antigen)

| | Antigen + Lectin | Antigen Only | Experimental % of Control |
|---|---|---|---|
| Torpedo receptor | 54 | 129 | 41 |
| Tetanus toxoid | 79 | 161 | 48 |
| Pneumococcal polysaccharide | 111 | 143 | 78 |

The effect of coadministration of lectin on the B-cell repertoire mounted as a primary response to immunization was also tested directly by antibody formation in the sera. Immunoassays for antibody content for the various antigens were performed as follows:

For immunization with Torpedo acetylcholine receptor, microtiter wells were coated overnight with 100 µl of a solution containing 5 µg/ml of purified receptor as prepared in Example 8, Part A, and incubated with serum (diluted 1/25) for 3 hours at 37° C. After washing, the plates were incubated for 3 hours at 37° C. with alkaline phosphatase-conjugated goat anti-mouse immunoglobulins. The plates were then washed extensively and incubated for 1 hour at 37° C. with p-phenylphosphate ethanolamine buffer. The reaction was stopped by addition of 25 µl of 3 M NaOH, and the binding of the labeled antibody was measured in an ELISA microreader at 405 nm. A normal mouse serum pool from more than 50 mice served as negative control. The cut-off limit was the mean +4SD of cumulated values obtained with this normal serum pool. The results were compared to results obtained by radioimmunoassay and expressed in moles of toxin receptor precipitated by 1 liter of serum, after subtraction of the mean ±4SD of cumulated results from a normal population (more than 50 mice).

For antibodies against mouse AChR, antibodies were determined using as antigen a complex between a partially purified normal mouse skeletal muscle receptor and $^{125}$I-alpha-bungarotoxin. The results were expressed in moles of toxin receptor precipitated by 1 liter of serum, after subtraction of the mean +4SD of cumulated results from a normal population (more than 50 mice).

For antibodies against tetanus toxoid and capsular polysaccharides, microtiter wells were coated overnight with 100 µl of a solution containing 5 µg/ml of the antigen and incubated with serum (diluted 1/200) for 3 hours at 37° C. After washing, the plates were incubated for 3 hours at 37° C. with alkaline phosphatase-conjugated goat anti-mouse immunoglobulins. The plates were then washed extensively and incubated for 1 hour at 37° C. with p-phenylphosphate ethanolamine buffer. The reaction was stopped by addition of 25 µl of 3 M NaOH, and the binding of the labeled antibody was measured in an ELISA microreader at 405 nm. A normal mouse serum pool from more than 50 mice served as negative control. The cut-off limit was the mean +4SD of cumulated values obtained with this normal serum pool. The values were expressed in milliabsorbance units after subtraction of the mean +4SD of the normal serum pool.

Groups of BALB/c mice were immunized with tetanus toxoid, pneumococcal polysaccharide, ray Torpedo receptor and mouse receptor without and with various doses of recombinant lectin. Blood was obtained after 3 days and again after 1, 2, 3 and 4 weeks and antibody levels were determined as described above.

The results are shown in FIGS. 6–9. As indicated, the primary immune response to T-dependent antigens was significantly lowered when higher doses of lectin (15 and 25 µg) were administered. No effect by any dose of the inventive lectin was observed for pneumococcal polysaccharide (FIG. 7), a T-independent antigen.

EXAMPLE 7

Effect of 14 kD β-gal Lectin on Experimental Autoimmune Encephalomyelitis, An Animal Model for Multiple Sclerosis Experimental autoimmune encephalomyelitis (EAE) is a T-cell-mediated disease considered to be a useful model for human paralytic and demyelinating diseases such as multiple sclerosis (Vandenbark, A. et al., *J. Immunol.* (1985) 135:223). In the Lewis rat, paralytic signs of EAE are induced about 14 days after injecting guinea pig myelin basic protein (GPBP) in Complete Freund's Adjuvant (CFA). It has been shown by Offner, H. et al. (*J. Immunol.* (1988) 141:3288) that T-cells specific for GPBP in immunized rats recognize amino acid residues 72–89 of GPBP and have the ability to transfer both clinical signs of EAE and delayed-type hypersensitivity reaction to GPBP to other animals.

In the studies reported in this example, EAE was induced by injection of GPBP/CFA as described above.

In one protocol intravenous administration of lectin was started at day 0 relative to 50 µg GPBP/CFA injection, with additional lectin treatment at days 3 and 6. The severity of the disease was determined clinically and histologically: "Clinical" ratings are as follows:

0=No signs of disease.
1=Flaccid tail.
2=Ataxia.
3=Hind quarter paralysis.
4=Quadriplegic/Moribund.

"Histologic" ratings are as follows:

Slides were examined for degree of inflammation with ratings as follows:

0=None;
0.5=a few infiltrating cells in the meninges;
1=meningeal infiltration, more organized and concentrated around blood vessels;
2–4=increasing intensity of meningeal infiltration and perivascular cuffing in the CNS parenchyma.

As shown in Table 5, the 0, 3, 6-day protocol resulted in a slight delay in the onset of sickness; the sickness was less severe; the duration of sickness was shorter; and weight loss was less.

TABLE 5

Treatment of EAE with Lectin

|  | Day of Onset | Severity of Disease Clinical/ Histological Ratings | Duration (days) | Loss of Weight (g) |
|---|---|---|---|---|
| Group I 10 control rats injected with buffer Days 0, 3, 6 | 14.5 | (3.2/—) | 4 | 30 |
| Group II 10 rats injected with 250 µg lectin Days 0, 3, 6 | 17 | (2.2/3.5) | 3.0 | 20 |

(p < .01)

In a second protocol, lectin was first administered three days before immunization with 50 µg GPBP/CFA and was followed by daily injections until day 7 after immunization. As shown in Table 6, with this protocol, the development of the disease was prevented completely.

TABLE 6

Treatment of EAE with Lectin

|  | Day of Onset | Severity of Disease Clinical/ Histologic | Duration (days) | Loss of Weight (g) | DTH[1] GPBP/PPD |
|---|---|---|---|---|---|
| Group I 20 control rats injected with buffer Days −3, −2, −1, 0, 1, 2, 3, 4, 5, 6 | 14 | 3.3/3.5 | 4.5 | 40 | 26/18 |
| Group II 10 rats injected with 250 µg lectin Days 0, 3, 6 | 17 | 2.2[2]/— | 3 | 20 | —/— |
| Group III 10 rats injected with 250 µg lectin Days −3, −2, −1, 0, 1, 2, 3, 4, 5, 6 | NA | 0[3]/0.50[3] | 0[3] | None[3] | 9[3]/4[3] |

[1]DTH = delayed type hypersensitivity reaction, which is reported as swelling × mm/100 (background subtracted)
[2]Difference from control has a p < 0.01
[3]Difference from control has a p < 0.001

In an additional experiment, animals were given various doses of lectin on days 0–12, following the administration of 10 µg GPBP injected intramuscularly. The results of these experiments are shown in FIGS. 10 and 11.

Figure 10:
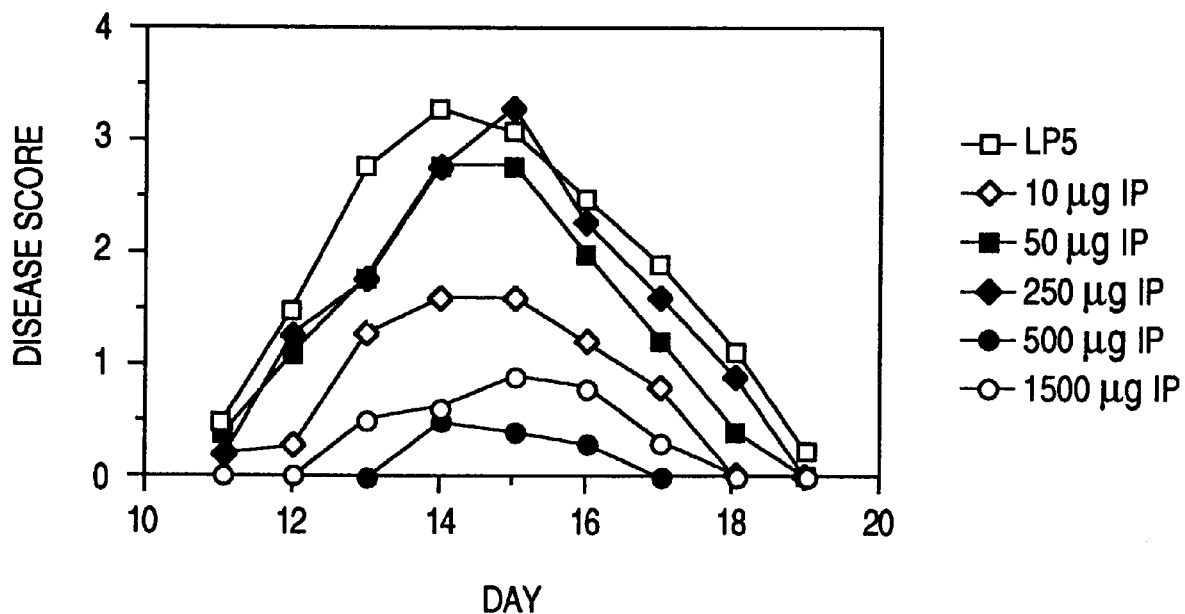
FIGS. 10 and 11 show the results of the treatment with the inventive lectin on clinical symptoms in a rat model for multiple sclerosis.
Figure 11:
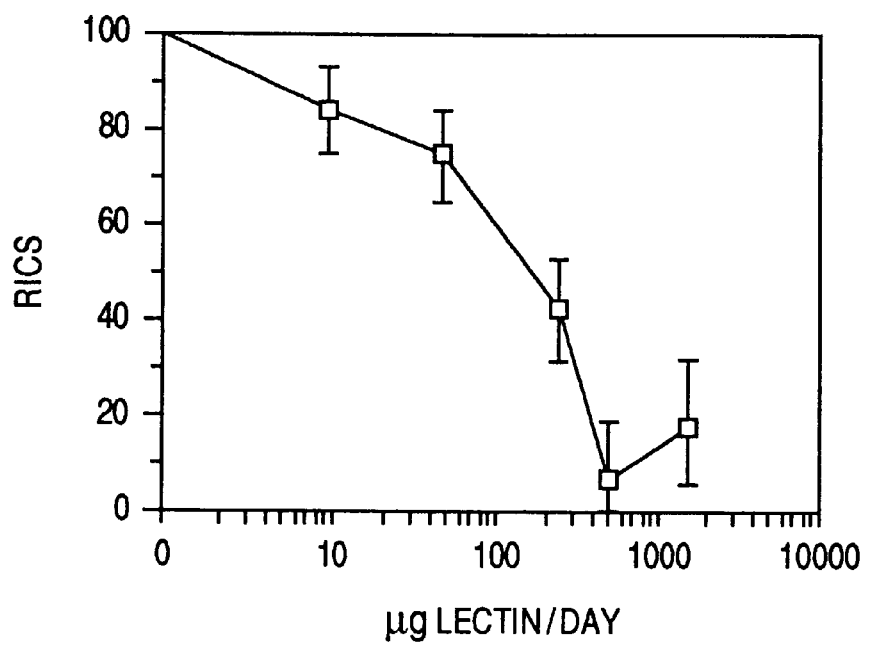

FIG. 10 shows the severity of the disease with lectin dosages ranging from 10–1500 µg intraperitoneally. FIG. 11 shows a summary representation of these results computed on day 12. As determined from FIGS. 10 and 11, a daily dosage of 500 µg appears optimal for ameliorating the symptoms of experimental autoimmune encephalitis.

EXAMPLE 8

Ability of Lectin to Prevent Primary Sensitization to GPBP and PPD Specifically

Figure 12:
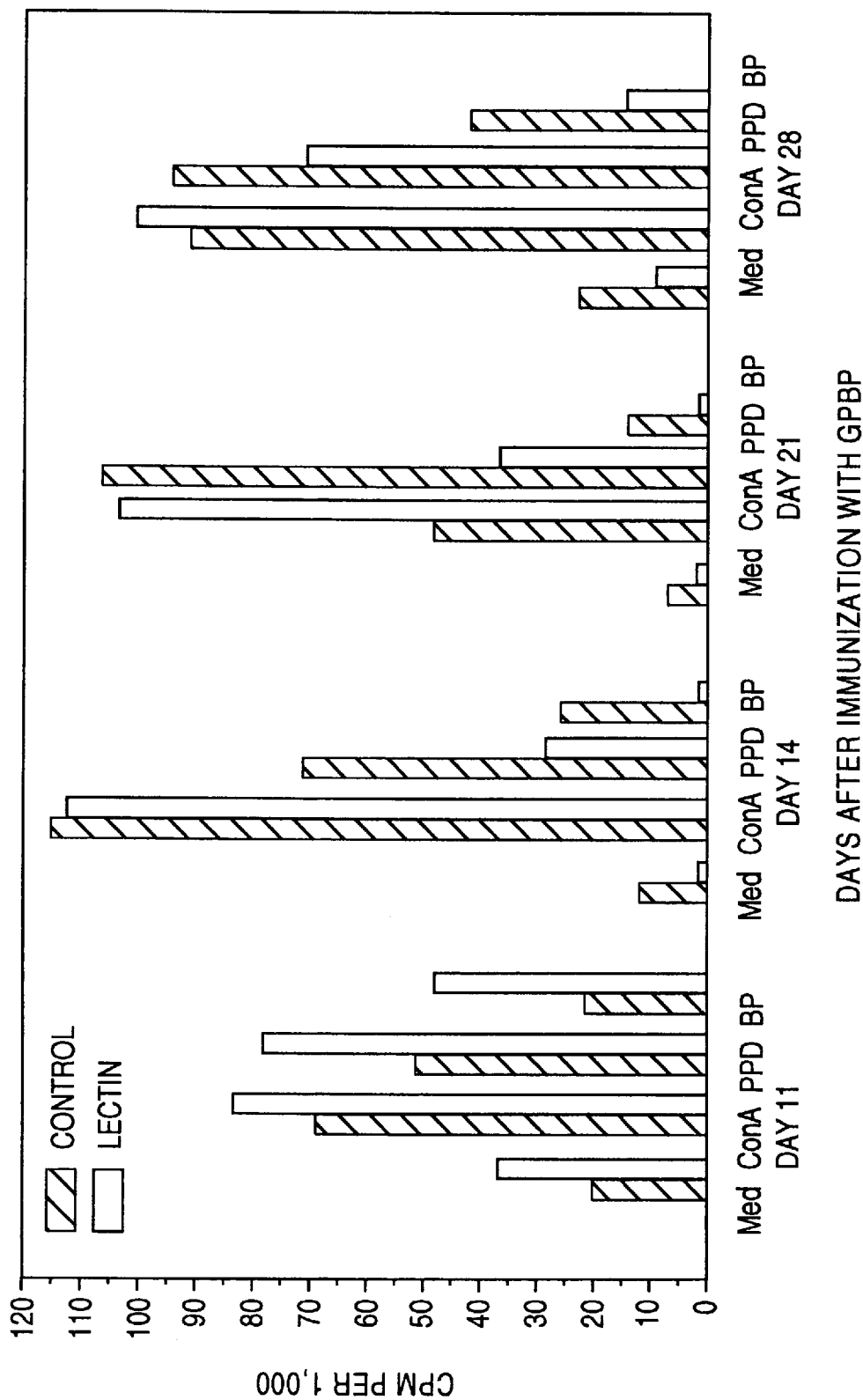
FIG. 12 is a graphical representation of the effect of recombinantly produced lectin in a rat model for multiple sclerosis.

At the indicated times after injection of 50 µg GPBP/CFA, lymph nodes draining the site of injection were collected and tested for a proliferative response to GPBP, purified protein derivative (PPD), and the T-cell mitogen, Concanavalin A (ConA). Consistent with the DTH test, lymph node cells of the lectin-treated rats had low or absent responses to both GPBP and PPD relative to control rats, especially on days 14 and 21 during which EAE onset occurs. Responses to ConA in treated rats were normal or augmented, however, indicating lack of global immunosuppression. These results are summarized in FIG. 12.

The lymph node cells were also unresponsive to the inventive lectin (data not shown), indicating that the lectin was not mitogenic. In addition, the sera of treated rats did not contain antibodies specific for the lectin as measured by ELISA.

In a follow-up experiment, T-cell lines were selected from the draining lymph nodes. Although GPBP-specific T-cell lines could be raised from the GPBP/CFA immunized control group, no responses were observed to GPBP and no lines could be established from the lectin-treated rats. In separate experiments, lectin added to established T-cell lines had no inhibitory effect, however. Taken together, the data show that the inventive recombinant lectin is potent in preventing primary sensitization to both GPBP and PPD, but did not affect T-cell responses generally, as shown by full T-cell responses to ConA.

EXAMPLE 9

Effect of the Inventive 14 kD Lectin on EAE Relapse

An additional murine model of EAE was used to demonstrate the effect of the inventive lectin on this condition.

In mice, symptoms of EAE can be made to occur in cyclical fashion by boosting the animals with antigen following each cycle, and each cycle becomes more severe until death ultimately occurs. This is a useful model in which to determine therapeutic efficacy, since it closely mimics both the chronic disease relapses and the acute demyelination associated with multiple sclerosis. In this experiment, 20 female SJL/J mice were immunized with lyophilized spinal cord extract dissolved in PBS plus CFA on days 0, 7 and 21. Ten mice were injected with recombinant lectin, and ten mice were given buffer only. The lectin-treated mice received 50 μg lectin on days 13 and 15 intravenously in the tail vein, and an additional 100 μg i.v. daily from day 18 through day 24. Mice were followed until death or sacrifice at day 42.

The results in FIG. 13 are mean clinical scores for control and lectin-treated mice. Lectin-treated mice had improved clinical scores during the first cycle, and improved survival and clinical scores through the second cycle.

EXAMPLE 10

Effect of Lectin Treatment on Transplant Acceptance and Rejection

The studies reported here relate to Brown Norway rat tissue transplanted into Lewis rats. This model, a highly histo-incompatible donor/recipient pair, provides a very stringent test with predictive value in human transplantation. Known general immunosuppressive agents show immunosuppressive activity in these models. Several forms of this model are used in the studies reported here.

A. Rat Heart Transplantation:

These studies were performed in the laboratory of Dr. Randy Morris of Stanford University. Whole rat hearts were grafted into host rats which were examined daily thereafter for signs of rejection. The treatment groups, dose and schedule of administration are summarized in Table 7.

TABLE 7

Heart Allograft Rejection

| No. Animals | Dose | Schedule | Onset of Rejection (day) |
|---|---|---|---|
| 2 | 1 mg/kg | d − 3 to d + 9 | 9.8 +/− .8 |
| 3 | 2 mg/kg | d − 3 to d + 9 | 9.8 +/− .8 |
| 12 | Control | d − 3 to d + 9 | 6.8 +/− .6 |

$p < .001$

A control group comprised twelve recipients treated daily i.v. only with buffer control. The graft survival times were: 6d (x4), 7d (x7), and 8d, giving a mean survival of 6.82+/−0.6d (SD). The final day of survival is defined as the day on which the donor heart ceased to contract as assessed by lack of obvious palpitations and as confirmed by direct visualization at laparotomy.

Five recipients were treated with the recombinant lectin. All animals were pretreated with 1 mg/kg i.v. lectin on days −3, −2 and −1. The first two animals were then treated postoperatively with 1 mg/kg/d i.v. with lectin from day 1 until graft rejection. The second three animals were treated in the postoperative period from day 1 until graft rejection with 2 mg/kg/d i.v. of lectin. Graft survivals were 9 and 10d for the first group of rats, and 9, 10 and 1ld for the second group. No dramatic increase in survival was seen by doubling the dose of lectin in group two in the post-operative period. Therefore, graft survival times of both groups were combined for statistical analysis. When graft survival was analyzed, lectin treatment produced a mean graft survival of 9.8+/−0.84d (SD), +/−0.38d (SEM) with a 95% confidence limit. Using the one-tailed Mann-Whitney U-test to compare the differences between the graft survival times for the saline and lectin-treated groups, a P value of 0.00096 was obtained.

Thus, a small but very highly significant prolongation of heart allograft survival was achieved by treatment with lectin. In addition, there was no noticeable toxicity as might be manifested by weight loss.

B. Effect of General Immunosuppressants in Combination with Lectin:

The heart transplant model of paragraph A was used. Five groups of 5 Lewis rats received hearts from Brown Norway rats and were given the following drugs by group, as shown in Table 8:

TABLE 8

| Group | Cyclosporin (mg/kg/day) | Lectin (mg/kg/Day) | Survivors on Day 16 |
|---|---|---|---|
| A | 0 | 2.5 | 0/5 |
| B | .75 | 1.0 | 3/5 |
| C | .75 | 2.5 | 5/6 |
| D | .75 | 5.0 | 5/5 |
| E | .75 | 0 | 2/3 |

Cyclosporin i.p. was started the day of the graft and continued daily. Recombinant lectin was started two days prior to transplant and continued daily.

The number of survivors on day 16 are shown in Table 8. The group receiving cyclosporin alone was unusually long lived, since animals on such therapy typically die within two weeks. At certain dosages of cyclosporin and lectin (2.5 and 5.0 mg/kg/day), the combination therapy had a higher survivor rate than cyclosporin or lectin administered alone or the sum of the two survival rates. After day 20, the differences between control and test groups decreased, which may be attributed to 1) the unusually longevity of the cyclosporin-treated rats and 2) the immunogenicity of human lectin in rats.

C. Skin Allografts:

The work in this report was done in the laboratory of Drs. Arthur Vandenbark and Halina Offner at the Oregon VA Medical Center. Brown Norway rat skin was transplanted onto the back of Lewis rats. Identical grafts were done on both sides of each animal's back and the results of each side (separated by commas) were shown for each parameter in Tables 9 and 10. The days upon which each graft exhibited inflammation, signs of degeneration, and finally rejection are given along with whether or not (+ or −) hair growth was restored in the tissue. A 250 μg/animal dose of lectin was administered i.v. daily on days 2–17. The results show that the lectin treatment delayed rejection of the grafts by 7 days, significantly reduced associated inflammation, and allowed the growth of hair in the grafted tissue.

The protocols for the studies reported in Tables 9 and 10 differed only in that the lectin was delivered for four additional days up to day 21 (see Table 10).

TABLE 9

| Control Animals No. | 1 | 2 | 3 | 4 | 5 | Mean + SD |
|---|---|---|---|---|---|---|
| Inflammation (on day) | 9,6 | 7,8 | 9,7 | −,6 | 10,− | |
| Degeneration (on day) | 10,6 | 8,10 | 10,7 | 13,8 | 10,8 | |
| Rejection (on day) | 13,6 | 8,11 | 11,7 | 16,8 | 13,10 | 10 ± 3 |
| Hair Growth | −,− | −,− | −,− | +,− | −,− | — |
| Histology | 4+ | 4+ | 3' | 4+ | 3' | |
| rIML-1 treated Day 2 to Day 17: | 1 | 2 | 3 | 4 | 5 | |
| Inflammation (on day) | −,− | −,− | −,− | −,− | −,− | |
| Degeneration (on day) | 15,16 | 11,13 | 14,− | −,− | −,16 | |
| Rejection (on day) | 16,17 | 13,15 | 16,16 | 18,18 | 18,18 | 17 ± 2 |
| Hair Growth | +,+ | −,+ | +,+ | +,+ | +,+ | + |
| Histology | 1+ | 1+ | 0 | + | 0 | |

TABLE 10

| Control Animal No. | 1 | 2 | 3 | 4 | | | Mean + SD |
|---|---|---|---|---|---|---|---|
| Inflammation (on day) | 6,− | −,10 | 6,− | 6,7 | | | |
| Degeneration (on day) | 6,11 | 6,10 | 6,12 | 7,11 | | | 8 ± 2 |
| Rejection (on day) | 7,13 | 8,12 | 11,14 | 9,12 | | | 10 ± 2 |
| Hair Growth | −,− | −,− | −,+ | −,− | | | |
| rIML-1 treated Day 2 to Day 21: | 1 | 2 | 3 | 4 | 5 | 6 | Mean + SD |
| Inflammation (on day) | −,− | −,+ | −,− | −,− | | | |
| Degeneration (on day) | 18,18 | 15,11 | 17,19 | 18,19 | 15,19 | 15,18 | 17 ± 2 |
| Rejection (on day) | 21,21 | 17,13 | 18,20 | 19,22 | 18,23 | 19,19 | 19 ± 2 |
| Hair Growth | +,+ | −,+ | +,+ | +,+ | +,+ | +,+ | + |

The results of similar experiments conducted by Dr. Ann Kari-Lefvert at the Karolinska Institute are reported in FIG. 14. In this experiment, 5 mg/kg recombinant lectin was used on rats bearing single grafts and the day of graft rejection was noted. As shown in FIG. 14, treatment with the inventive lectin considerably delayed rejection of the skin allograft.

EXAMPLE 11

In Vivo Effect of Lectin On Phenotypes of Selected Rat Lymphocytes

Table 11A shows a 28% increase in the number of rat lymph node suppressor T-cells (reactive with monoclonal antibody OX8, Serotec-Bioproducts, Indianapolis, Ind.) from lectin-treated animals.

Table 11B shows a 32% increase in the number of spleen suppressor T-cells as well as a 19% and 24% decrease in the numbers of helper T-cells (w3/25 antibody reactive, Serotec-Bioproducts) and total T-cells (w3/13 antibody reactive, Serotec-Bioproducts), respectively.

TABLES 11A and 11B

In Vivo Effect of Lectin-Treated Rats on Phenotypes of Selected Lymphocytes

| | CONTROL | | | LECTIN | | | % CHANGE |
|---|---|---|---|---|---|---|---|
| Antibody | $F^L$ | % positive | % | $F^L$ | % positive | % | IN POSITIVES |
| 11A. Lymph Node Cells | | | | | | | |
| IgG | 131 | 15.9 | — | 129 | 16.4 | — | — |
| W3/13 | 443 | 99.5 | 83.6 | 442 | 99.5 | 83.1 | 0 |
| W3/25 | 216 | 78.1 | 62.2 | 230 | 76.5 | 60.1 | −0 |
| OX8 | 448 | 26.7 | 10.8 | 472 | 30.3 | 13.9 | +28 |
| OX6 | 1141 | 8.5 | 0 | 1208 | 10.0 | 0 | 0 |
| OX12 | 340 | 9.4 | 0 | 316 | 9.9 | 0 | 0 |
| 11B. Spleen Cells | | | | | | | |
| IgG | 123 | 22.5 | — | 129 | 24.3 | — | — |
| W3/13 | 334 | 98.5 | 76.0 | 311 | 85.9 | 61.7 | −19 |
| W3/25 | 195 | 79.2 | 56.7 | 161 | 67.2 | 43.0 | −24 |

TABLES 11A and 11B-continued

In Vivo Effect of Lectin-Treated Rats on Phenotypes of Selected Lymphocytes

| Antibody | CONTROL | | | LECTIN | | | % CHANGE IN POSITIVES |
|---|---|---|---|---|---|---|---|
| | $F^L$ | % positive | % | $F^L$ | % positive | % | |
| OX8 | 311 | 35.4 | 12.9 | 323 | 41.2 | 17.0 | +32 |
| OX6 | 720 | 14.6 | 0 | 375 | 15.6 | 0 | 0 |
| OX12 | 262 | 14.9 | 0 | 363 | 15.4 | 0 | 0 |

EXAMPLE 12

Human blood cells were pretreated with the inventive HL-60 lectin and then stained with fluoresceinated antibody having several different specificities. Control cells were not pretreated with lectin. The results in Table 12 show that recombinant human lectin specifically reacts with human macrophages. No significant changes were observed for CD3+, CD4+, NK(L-A) or HLA-DR cell markers (Becton-Dickinson). However, the effect of lectin treatment on M1 and M3 macrophages was significant. The percent of positive cells was reduced by 33% and 26%, respectively, suggesting an interaction between lectin and epitopes recognized by M1 and M3 antibodies.

TABLE 12

Histogram Analyses

| | Control | | | Lectin | | |
|---|---|---|---|---|---|---|
| | +FL1 | +mode | percent | +FL1 | +mode | percent |
| CD3+ | 624 | 620 | 76.4 | 458 | 416 | 77.8 |
| CD4+ | 257 | 234 | 40 | 181.5 | 151 | 46.4 |
| NK(L-A) | 169 | 157 | 10.8 | 106 | 94.7 | 10.8 |
| HLA-DR | 673 | 417 | 16.3 | 614 | 432 | 13.3 |

TABLE 12-continued

Histogram Analyses

| | Control | | | Lectin | | |
|---|---|---|---|---|---|---|
| | +FL1 | +mode | percent | +FL1 | +mode | percent |
| M1 | 345 | 323 | 79.5 | 403 | 387 | 46.1 |
| M3 | 575 | 556 | 70.7 | 549 | 517 | 45.1 |

What is claimed is:

1. A method of delivering drugs to cells of a mammalian subject, said cells having chemical moieties specific for an HL-60 lectin, the method comprising:
    coupling a lectin consisting of an amino acid sequence of positions 2–135 of FIG. 1 to a drug to form a lectin-drug complex; and
    administering said lectin-drug complex to the mammalian subject;
    wherein the lectin-drug complex selectively binds to cells having chemical moieties specific for the HL-60 lectin.
2. The method of claim 1, wherein the mammalian subject is a human.

* * * * *

UNITED STATES PATENT AND TRADEMARK OFFICE
CERTIFICATE OF CORRECTION

PATENT NO: 6,153,195
DATED: November 28, 2000
INVENTOR(S): Seilhamer et al.

It is certified that error appears in the above-identified patent and that said Letters Patent are hereby corrected as shown below:

On the title page
Please correct the spelling of inventor Jeffrey J. Seilhamer's name from "Jeffrey J. Seilhammer" to -- Jeffrey J. Seilhamer --.

Signed and Sealed this

First Day of May, 2001

*Attest:*

NICHOLAS P. GODICI

*Attesting Officer*   *Acting Director of the United States Patent and Trademark Office*